(12) United States Patent
Kurauchi

(10) Patent No.: US 12,005,023 B2
(45) Date of Patent: Jun. 11, 2024

(54) GAIT MOTION ASSISTING APPARATUS

(71) Applicant: Suncall Corporation, Kyoto (JP)

(72) Inventor: Yukari Kurauchi, Kyoto (JP)

(73) Assignee: Suncall Corporation, Kyoto (JP)

( * ) Notice: Subject to any disclaimer, the term of this patent is extended or adjusted under 35 U.S.C. 154(b) by 743 days.

(21) Appl. No.: 17/273,081

(22) PCT Filed: Sep. 9, 2019

(86) PCT No.: PCT/JP2019/035295
§ 371 (c)(1),
(2) Date: Mar. 3, 2021

(87) PCT Pub. No.: WO2020/079988
PCT Pub. Date: Apr. 23, 2020

(65) Prior Publication Data
US 2021/0315766 A1    Oct. 14, 2021

(30) Foreign Application Priority Data

Oct. 18, 2018  (JP) ................................ 2018-196364

(51) Int. Cl.
*A61H 3/00*   (2006.01)
*A61H 1/02*   (2006.01)

(52) U.S. Cl.
CPC .............. *A61H 3/00* (2013.01); *A61H 1/024* (2013.01); *A61H 1/0266* (2013.01);
(Continued)

(58) Field of Classification Search
CPC ........ A61H 3/00; A61H 1/024; A61H 1/0266; A61H 2003/007; A61H 2201/1215;
(Continued)

(56) References Cited

U.S. PATENT DOCUMENTS

2020/0069505 A1   3/2020  Fujita et al.
2020/0315899 A1  10/2020  Takahashi et al.

FOREIGN PATENT DOCUMENTS

EP        3 725 282 A1   10/2020
JP        2014124297 A    7/2014
(Continued)

OTHER PUBLICATIONS

Extended European Search Report issued in European Application No. 19874598.6, dated Mar. 21, 2022, 9 pages.
(Continued)

*Primary Examiner* — Jerrah Edwards
*Assistant Examiner* — Aren Patel
(74) *Attorney, Agent, or Firm* — Sterne, Kessler, Goldstein & Fox P.L.L.C.

(57) ABSTRACT

A gait motion assisting apparatus of the present invention can be connected to a knee-ankle-foot orthosis at three different positions in a vertical direction by upper, intermediate and lower connecting mechanisms. The intermediate connecting mechanism includes a ball stud arranged at the knee-ankle-foot orthosis extending outward in the user width direction on a brace-side pivot axis line X and an accommodation depression opened toward the knee-ankle-foot orthosis on the actuator-side pivot axis line Y so that the ball stud can be inserted thereinto. The accommodation depression is arranged at an innermost power-transmitting member among a driving arm and components of a transmission mechanism operatively transmitting rotational power from an electric motor to the driving arm.

9 Claims, 17 Drawing Sheets

(52) U.S. Cl.
CPC .............. *A61H 2003/007* (2013.01); *A61H 2201/1215* (2013.01); *A61H 2201/14* (2013.01); *A61H 2201/1642* (2013.01); *A61H 2201/1671* (2013.01); *A61H 2201/1676* (2013.01); *A61H 2201/5064* (2013.01); *A61H 2201/5069* (2013.01); *A61H 2201/5084* (2013.01); *A61H 2205/102* (2013.01); *A61H 2205/106* (2013.01); *A61H 2205/12* (2013.01); *A61H 2230/625* (2013.01)

(58) Field of Classification Search
CPC ........ A61H 2201/14; A61H 2201/1642; A61H 2201/1676; A61H 2201/5064; A61H 2201/5069; A61H 2201/5084; A61H 2205/102; A61H 2205/106; A61H 2205/12; A61H 2230/625
See application file for complete search history.

(56) References Cited

FOREIGN PATENT DOCUMENTS

| | | | |
|---|---|---|---|
| JP | 6148766 | B1 | 6/2017 |
| JP | 2017-140303 | A | 8/2017 |
| JP | 6766117 | B2 | 10/2020 |
| WO | 2017208851 | A1 | 11/2017 |
| WO | 2018158968 | A1 | 9/2018 |

OTHER PUBLICATIONS

International Search Report issued in International Application No. PCT/JP2019/035295, dated Nov. 26, 2019, 4 pages.
Office Action issued in JP Application No. 2018-196364, dated Jun. 5, 2020, 6 pages.

 ...

GAIT MOTION ASSISTING APPARATUS

FIELD OF THE INVENTION

The present invention relates to a gait motion assisting apparatus imparting gait assisting force to a user that wears a knee-ankle-foot orthosis.

BACKGROUND ART

There are conventionally proposed gait motion assisting apparatuses attachable to knee-ankle-foot orthoses that are utilized as gait assistance or rehabilitation devices for people with leg disability or people with paralysis due to a stroke or the like (see Patent Literature 1 below).

Specifically, knee ankle foot orthoses include a thigh attachment to be attached to a user's thigh, a thigh frame vertically extending while substantially supporting the thigh attachment, a lower leg attachment to be attached to the user's lower leg and a lower leg frame vertically extending while supporting the lower leg attachment, wherein the lower leg frame is rotatable around a brace-side pivot axis line that is coaxial with the user's knee joint relative to the thigh frame.

The gait motion assisting apparatus includes a casing, an electric motor accommodated in the casing, a driving arm driven around a driving-side pivot axis line by a driving rotational force operatively transmitted via a transmission mechanism from an output shaft of the electric motor, an upper connecting mechanism for connecting an upper portion of the casing to the thigh frame, a lower connecting mechanism for operatively connecting a distal end portion of the driving arm to the lower leg frame, and an intermediate connecting mechanism for having the driving-side pivot axis line coincided with the brace-side pivot axis line.

The intermediate mechanism includes a tubular convex portion provided in the knee ankle foot orthosis so as to extend outward in the user width direction on the brace-side pivot axis line, and an accommodation depression provided in the gait motion assisting apparatus so as to be opened toward the knee ankle foot orthosis in such a manner that the tubular convex portion can be inserted into the accommodation depression.

In the conventional gait motion assisting apparatus, the driving arm is supported by a driving shaft arranged coaxially with the driving-side pivot axis line.

Specifically, the driving shaft has a first end portion supported by an inner wall of the casing that is opposed to the knee ankle foot orthosis and a second end portion supported by an outer wall of the casing that is far from the knee ankle foot orthosis.

The driving arm has a proximal end portion supported by an intermediate portion of the driving shaft between the first and second end portions so as to be incapable of relative rotation, and the distal end portion extending downward through a slit formed in the casing and operatively connected to the lower leg frame.

The accommodation depression is formed in a fixed plate that is fixed to an outer surface of the inner wall.

The thus configured conventional gait motion assisting apparatus is useful in that it can be connected to the knee-ankle-foot orthosis in a state where the intermediate connecting mechanism has the driving-side pivot axis line arranged coaxially with the brace-side pivot axis line without fault. However, it is needed that the inner wall of the casing is provided with a bearing structure for supporting the first end portion of the driving shaft. Moreover, it is difficult that the gait motion assisting apparatus is made thin because it is needed that the fixed plate is fixed to the outer surface of the inner wall of the casing for securing such a thickness as to allow the accommodation depression to be formed.

Furthermore, because the proximal end portion of the driving arm is supported by the intermediate portion of the driving shaft between the first and second ends that are supported by the inner and outer walls, respectively, a length in the in the user width direction between the proximal end portion of the driving arm and the lower leg frame is elongated. It causes another problem in which a larger driving torque is needed for pressing the lower leg frame.

PRIOR ART DOCUMENT

Patent Literature

Patent Literature 1: JP 6148766

SUMMARY OF THE INVENTION

The present invention has been conceived in view of such conventional art, and an object of the present invention is to provide a gait motion assisting apparatus capable of being attached to a knee-ankle-foot orthosis wherein a lower leg frame is connected to a thigh frame so as to be relatively rotatable around a brace-side pivot axis line that is coaxial with a swing axis line of the user's knee joint, the gait motion assisting apparatus including a casing, an electric motor housed in the casing and a driving arm having a proximal end portion rotated around an actuator-side pivot axis line by rotational power operatively transmitted from the electric motor and a distal end portion operatively connected to the lower leg frame of the knee-ankle-foot orthosis to press the lower leg frame around the brace-side pivot axis line, wherein the gait motion assisting apparatus can reduce the size in the user width direction as much as possible and also reduce the driving torque to be needed for pressing the lower leg frame as much as possible while it can be attached to the knee-ankle-foot orthosis with having the actuator-side pivot axis line reliably positioned coaxially with the brace-side pivot axis line.

In order to achieve the object, the present invention provides a gait motion assisting apparatus attachable to a knee-ankle-foot orthosis including a thigh attachment to which a user's thigh is attached, a thigh frame supporting the thigh attachment and extending in a substantially vertical direction, a lower leg attachment to which the user's lower leg is attached and a lower leg frame supporting the lower leg attachment and extending in a substantially vertical direction, the lower leg frame being rotatable relative to the thigh frame around a brace-side pivot axis line that is coaxial with a swing axis line of the user's knee joint, the gait motion assisting apparatus including an electric motor, a casing housing the electric motor, a driving arm driven and rotated around an actuator-side pivot axis line by rotational power operatively transmitted via a transmission mechanism from an output shaft of the electric motor, an upper connecting mechanism connecting an upper part of the casing to the thigh frame, a lower connecting mechanism operatively connecting a distal end portion of the driving arm to the lower leg frame, and an intermediate connecting mechanism having the actuator-side pivot axis line Y arranged coaxially with the brace-side pivot axis line X, wherein the intermediate connecting mechanism includes a ball stud arranged at the knee-ankle-foot orthosis so as to extend outward in the user width direction on the brace-side pivot axis line X and an accommodation depression arranged so as to open toward the knee-ankle-foot orthosis on the actuator-side pivot axis line, the ball stud capable of being inserted into the accommodation depression, and wherein the accommodation depression is arranged at an innermost power-transmitting member among components forming the transmission mechanism and the driving arm that is arranged coaxially with the actuator-side pivot axis line and is accessible from the inner side in the user width direction.

Since the gait motion assisting apparatus according to the present invention is configured so that it can be connected to the knee-ankle-foot orthosis at three different positions in the vertical direction by the upper connecting mechanism, the intermediate connecting mechanism and the lower connecting mechanism, the intermediate connecting mechanism includes the ball stud arranged at the knee-ankle-foot orthosis so as to extend outward in the user width direction on the brace-side pivot axis line X and the accommodation depression that is opened toward the knee-ankle-foot orthosis on the actuator-side pivot axis line and into which the ball stud can be inserted, and the accommodation depression is arranged at an innermost power-transmitting member among components forming the transmission mechanism and the driving arm that is arranged coaxially with the actuator-side pivot axis line and is accessible from the inner side in the user width direction, the gait motion assisting apparatus makes it possible to reduce the size in the user width direction as much as possible and also reduce the driving torque to be needed for pressing the lower leg frame as much as possible while it can be attached to the knee-ankle-foot orthosis with having the actuator-side pivot axis line reliably positioned coaxially with the brace-side pivot axis line.

In one embodiment, the casing includes a frame supporting the electric motor and a cover defining an accommodating space for the electric motor and the frame.

The cover includes a lower cover whose outer surface forms a facing surface facing the thigh frame in an attached state where the gait motion assisting apparatus is attached to the knee-ankle-foot orthosis and an upper cover detachably connected to the lower cover so as to form the accommodating space in cooperation with the lower cover.

The frame includes a vertical-direction extending wall extending substantially vertically in the attached state of the gait motion assisting apparatus and fixed to the lower cover. The electric motor includes a motor body supported by the frame and an output shaft extending downward from the motor body. The transmission mechanism includes a driving-side bevel gear supported by the output shaft so as to be incapable of relative rotation and a driven-side bevel gear that is positioned on a side more inward in the user width direction than the output shaft and arranged coaxially with the actuator-side pivot axis line while being engaged with the driving-side bevel gear.

The driving arm has a proximal end portion operatively connected to the driven-side bevel gear. The lower cover is provided with an access opening that allows the driven-side bevel gear and the proximal end portion of the driving arm to be connected to each other. The accommodation depression is arranged at an inward surface of the proximal end portion of the driving arm in the user width direction.

In a preferable configuration, the upper connecting mechanism may include an upper rotational shaft extending inward in the user width direction, an upper receiving member spaced apart in the user front-back direction from the upper rotational shaft by a distance that enables the thigh frame to be interposed between the upper receiving member and the upper rotational shaft, and an upper fastening member rotatably supported by the upper rotational shaft so as to take a releasing position and a fastening position around the upper rotational shaft.

The upper fastening member includes a bearing part supported by the upper rotational shaft and a cam part extending radially outward from the bearing part. Setting the upper fastening member in the releasing position enables the thigh frame to be entered into and retreated from the space, and rotating the upper fastening member from the releasing position to the fastening position in the state where the thigh frame is positioned in the space causes the cam part to hold the thigh frame in cooperation with the upper receiving member.

In a preferable configuration, the upper rotational shaft and the upper receiving member are supported by the vertical-direction extending wall.

In this configuration, the lower cover is formed with a through hole that allows distal end portions of the upper rotational shaft and the upper receiving member to extend outward in a direction toward the knee-ankle-foot orthosis.

In a more preferable configuration, the vertical-direction extending wall is capable of supporting the upper rotational shaft and the upper receiving member at a plurality of supporting positions that are displaced in the vertical direction.

In a more preferable configuration, the gait motion assisting apparatus according to the present invention may further include a plate capable of supporting the upper rotational shaft and the upper receiving member, and the vertical-direction extending wall is configured to support the plate at the plurality of supporting positions.

In a more preferable configuration, the lower cover is formed with the plurality of through holes corresponding to the plurality of supporting positions, respectively.

In this configuration, remaining through holes other than the through hole that is used for attaching the upper connecting mechanism are closed by closing plates.

In any one of the above various configurations, the lower connecting mechanism may preferably include a lower rotational shaft extending inward in the user width direction, a lower receiving member spaced apart in the user front-back direction from the lower rotational shaft by a distance that enables the lower leg frame to be interposed between the lower receiving member and the lower rotational shaft, and lower fastening member rotatably supported by the lower rotational shaft so as to take a releasing position and a fastening position around the lower rotational shaft.

The lower fastening member includes a bearing part supported by the lower rotational shaft and a cam part extending radially outward from the bearing part. Setting the lower fastening member in the releasing position enables the lower leg frame to be entered into and retreated from the space, and rotating the lower fastening member from the releasing position to the fastening position in the state where the lower leg frame is positioned in the space causes the cam part to hold the lower leg frame in cooperation with the lower receiving member.

In any one of the above various configurations, the gait motion assisting apparatus according to the present invention may preferably include a swinging member capable of swinging around a rotational shaft along the user front-back direction in a state where the gait motion assisting apparatus is attached to the knee-ankle-foot orthosis.

In this configuration, the lower connecting mechanism is supported by the swinging member.

EMBODIMENT FOR CARRYING OUT THE INVENTION

Below, one embodiment of the gait motion assisting apparatus according to the present invention will now be described with reference to the attached drawings.

The gait motion assisting apparatus 100A according to the present embodiment imparts gait assisting force to a user wear a knee-ankle-foot orthosis 1.

The knee-ankle-foot orthosis 1 is a device to be worn by a person with leg disability or a person with paralysis due to a stroke or the like for gait assistance or for rehabilitation, and is custom-made according to the user's physique.

First, the configuration of the knee-ankle-foot orthosis 1 will now be described.

Figure 1:
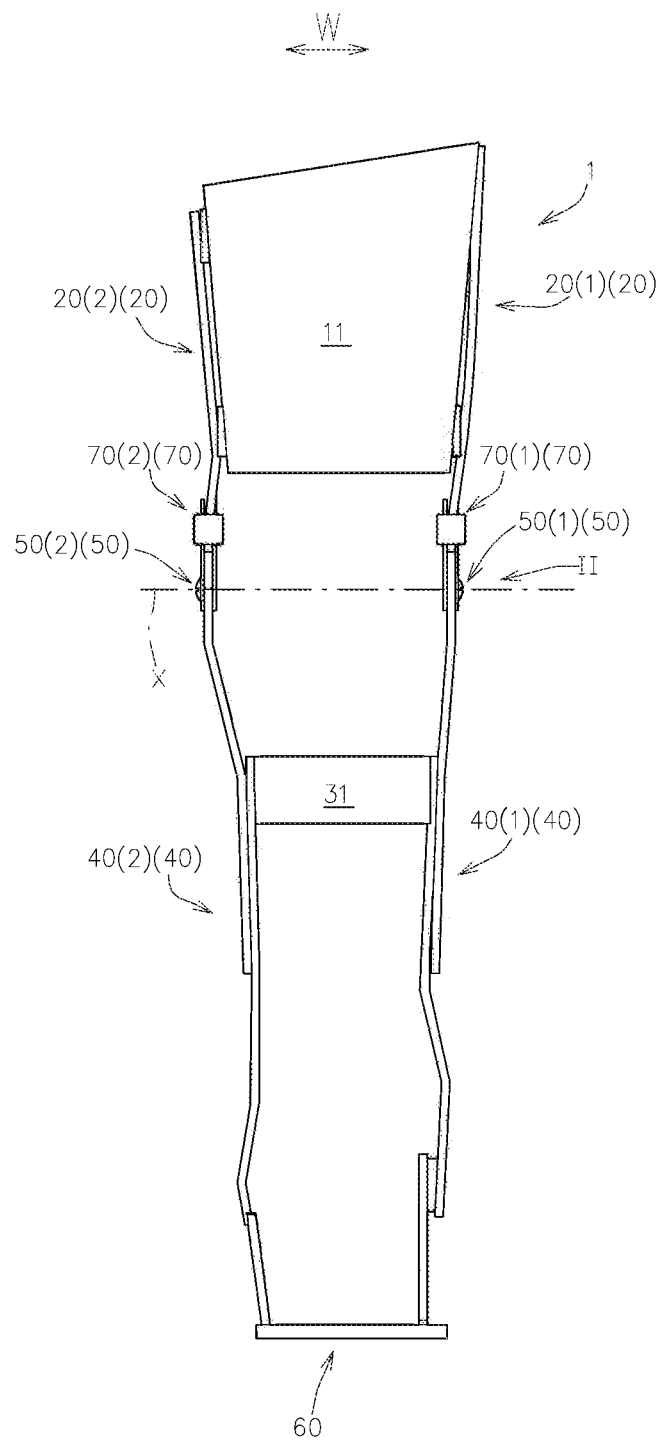
FIG. 1 is a front view of the knee-ankle-foot orthosis to which a gait motion assisting apparatus according to the present invention is attachable.

FIG. 1 is a front view of the knee-ankle-foot orthosis 1.

The knee-ankle-foot orthosis 1 shown in FIG. 1 is for left use that is attached to the user's left leg.

The knee-ankle-foot orthosis for right use is symmetrical to the knee-ankle-foot orthosis for left use with respect to a central vertical plane passing a body axis of the user and extending in the users front-back direction.

The knee-ankle-foot orthosis 1 is a device that is custom-made according to the user's physique.

Specifically, As shown in FIG. 1, the knee-ankle-foot orthosis 1 has a thigh attachment 11 to which the user's thigh is attached, a thigh frame 20 supporting the thigh attachment 11 and extending in a substantially vertical direction, a lower leg attachment 31 to which the user's lower leg is attached, and a lower leg frame 40 supporting the lower leg attachment 31 and extending in a substantially vertical direction.

The thigh attachment 11 and the lower leg attachment 31 may take various forms as long as they are respectively attachable to the user's thigh and lower leg.

In the present embodiment, the thigh attachment 11 is in a cylindrical form having an attachment hole with such a size that the user's thigh can be inserted and the thigh attachment 11 fits the thigh.

Likewise, the lower leg attachment 31 is in a cylindrical form having an attachment hole with such a size that the user's lower leg can be inserted and the lower leg attachment 31 fits the lower leg.

In the present embodiment, as shown in FIG. 1, the thigh frame 20 has a first thigh frame 20(1) vertically extending on the outer side of the thigh attachment 11 in the user width direction, and a second thigh frame 20(2) vertically extending on the inner side of the thigh attachment 11 in the user width direction.

Likewise, the lower leg frame 40 has a first lower leg frame 40(1) vertically extending on the outer side of the lower leg attachment 31 in the user width direction, and a second lower leg frame 40(2) vertically extending on the inner side of the lower leg attachment 31 in the user width direction.

Figure 2:
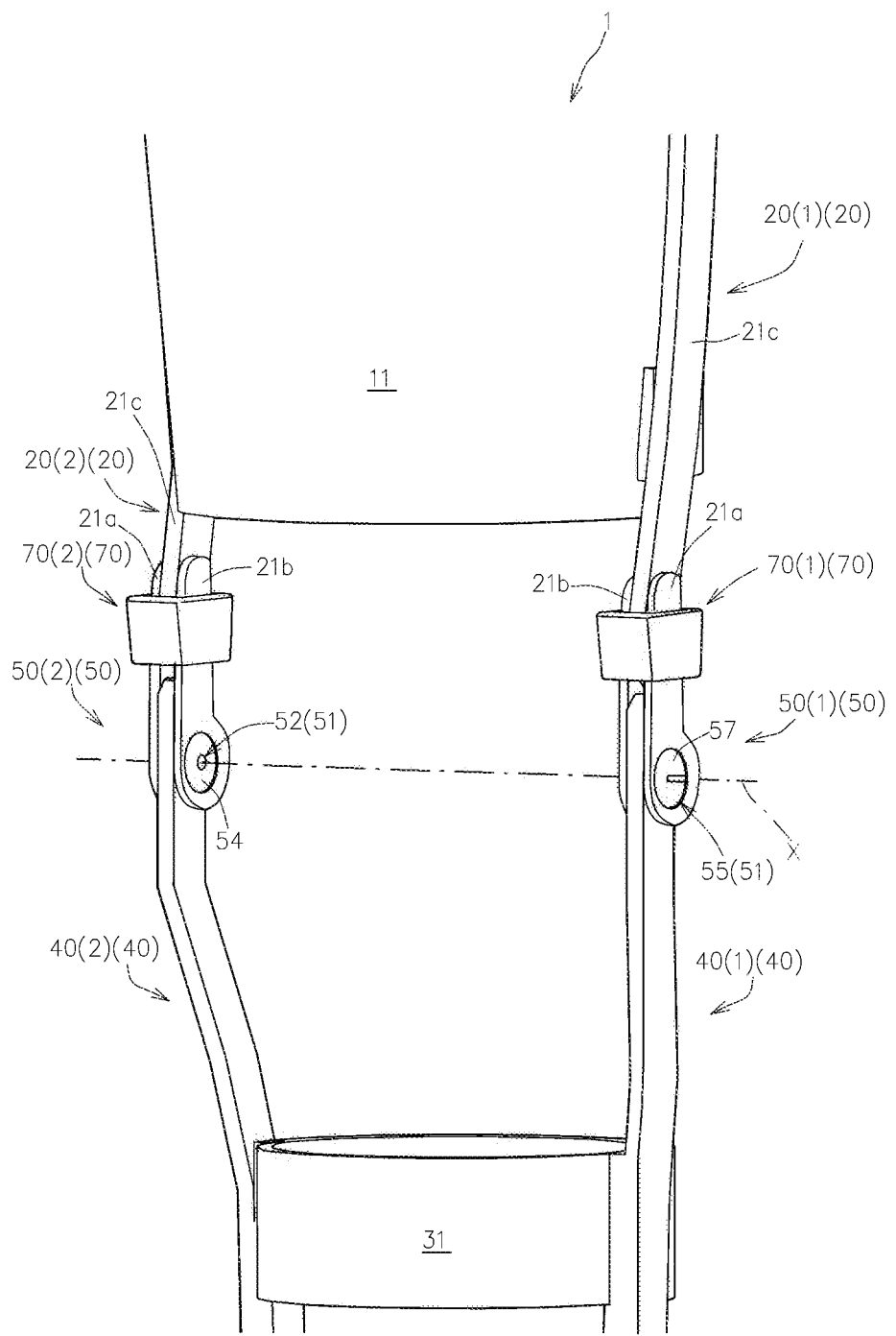
FIG. 2 is a perspective enlarged view of the II part in FIG. 1.

FIG. 2 shows a perspective enlarged view of the II part in FIG. 1.

Figure 3:
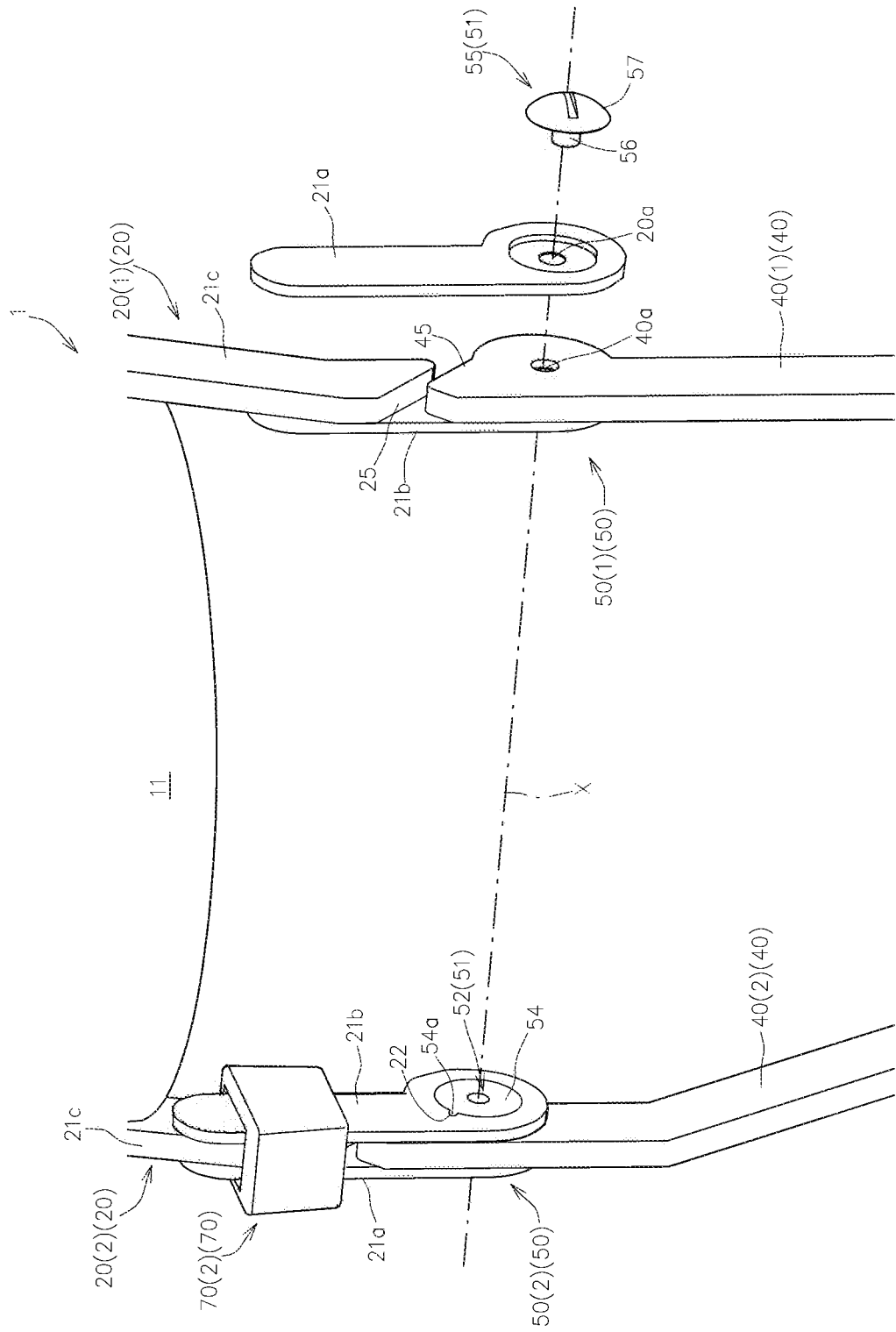
FIG. 3 is an exploded view of FIG. 2.

FIG. 3 shows an exploded view of FIG. 2.

Figure 6:
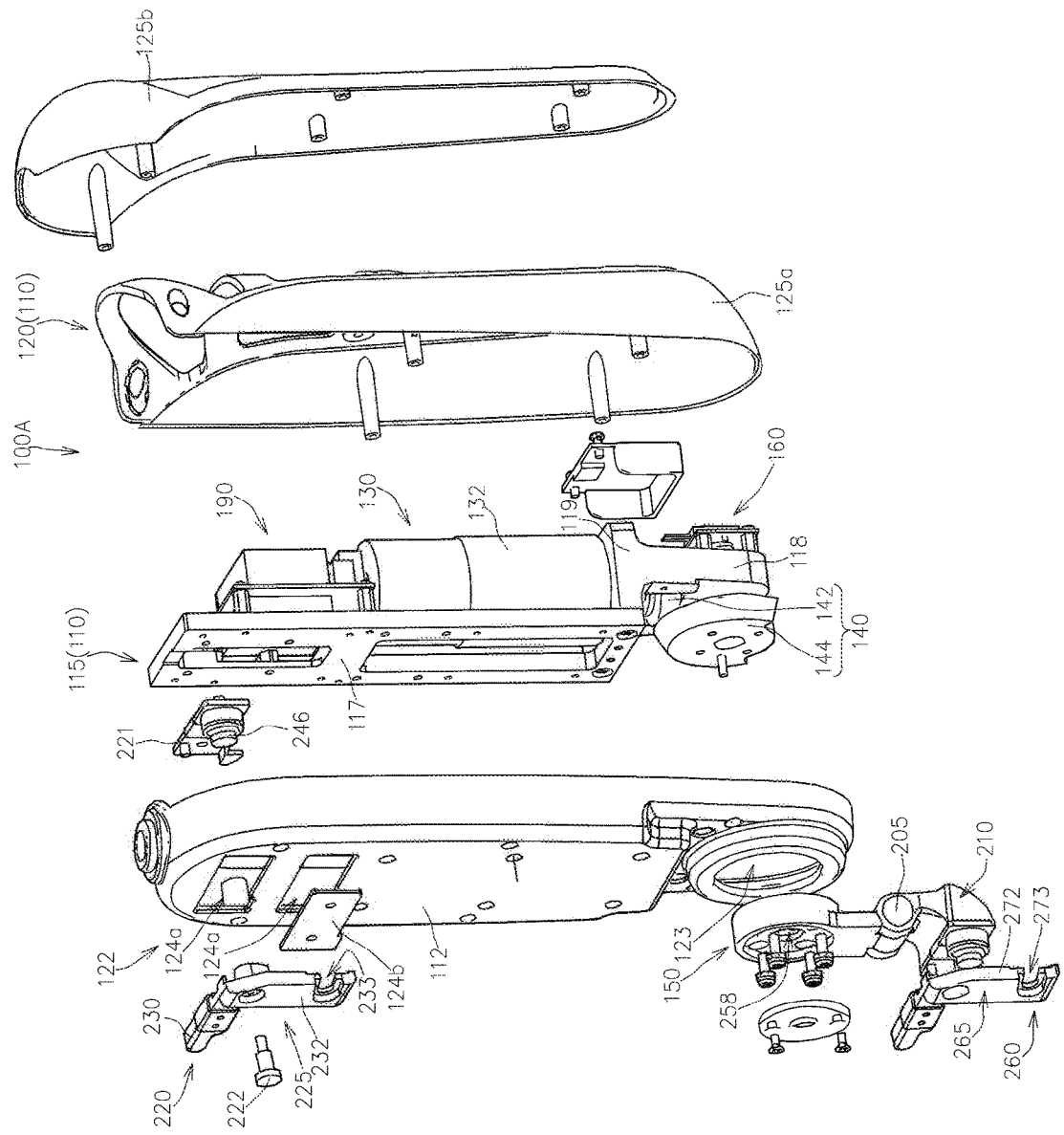
FIG. 6 is an exploded perspective view of the gait motion assisting apparatus as viewed from a side facing the knee-ankle-foot orthosis (the inner side in the user width direction).

In FIG. 6, illustration of a part of components is omitted for easier understanding.

Figure 4:
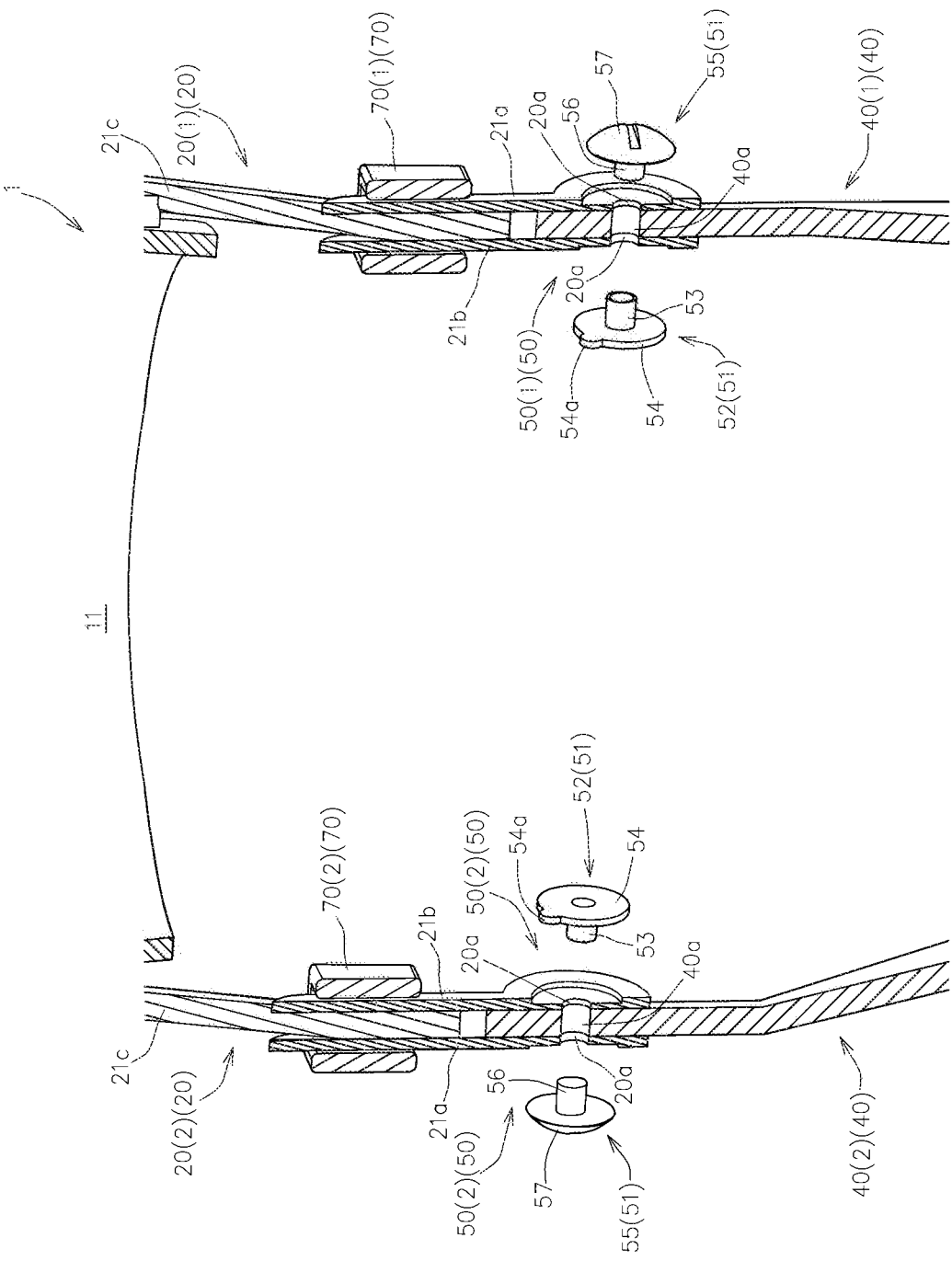
FIG. 4 is a vertical cross-sectional front view of FIG. 2.

FIG. 4 shows a vertical cross-sectional front view of FIG. 2.

As shown in FIGS. 1 to 4, the lower leg frame 40 is connected to the thigh frame 20 via a brace-side rotational connecting part 50 such that the lower leg frame 40 is rotatable relative to the thigh frame 20 around a brace-side pivot axis line X that is coaxial with the swing axis line of the user's knee joint.

As described above, in the present embodiment, the thigh frame 20 has the first and second thigh frames 20(1), 20(2), and the lower leg frame 40 has the first and second lower leg frames 40(1), 40(2).

In this case, an upper end portion of the first lower leg frame 40(1) is connected to a lower end portion of the first thigh frame 20(1) via a first brace-side rotational connecting part 50(1) so that the first lower leg frame 40(1) is rotatable around the brace-side pivot axis line X relative to the first thigh frame 20(1), and an upper end portion of the second lower leg frame 40(2) is connected to a lower end portion of the second thigh frame 20(2) via a second brace-side rotational connecting part 50(2) so that the second lower leg frame 40(2) is rotatable around the brace-side pivot axis line X relative to the second thigh frame 20(2).

Specifically, as shown in FIGS. 2 to 4, the thigh frame 20 has a vertically extending thigh frame main body 21c and a pair of connecting pieces 21a, 21b fixed to the respective sides in the user width direction of the lower end part of the frame main body 21c by pinning, welding, or the like. The upper part of the lower leg frame 40 is interposed between the pair of connecting pieces 21a, 21b.

The pair of connecting pieces 21a, 21b are provided with a thigh frame attachment hole 20a that is coaxially with the brace-side pivot axis line X, and the lower leg frame 40 is provided with a lower leg frame attachment hole 40a that is coaxially with the brace-side pivot axis line X.

The brace-side rotational connecting part 50 has a brace-side connector 51 for connecting the thigh frame 20 and the corresponding lower leg frame 40 so as to be rotatable around the brace-side pivot axis line X by being inserted into a brace-side frame attachment hole formed by the thigh frame attachment hole 20a and the lower leg frame attachment hole 40a.

As shown in FIGS. 2 to 4, the brace-side connector 51 has an internally threaded member 52 and an externally threaded member 55 separably screwed to each other within the brace-side frame attachment hole.

The internally threaded member 52 has a cylindrical part 53 to be inserted into the brace-side frame attachment hole from one side in the user width direction and a flange part 54 extending more radially outward than the brace-side frame attachment hole from one side in the user width direction of the cylindrical part 53. The cylindrical part 53 has a screw hole that is open toward the free end side.

On the other hand, the externally threaded member 55 has a cylindrical part 56 having an external thread to be screwed into the screw hole from the other side in the user width direction and a flange part 57 extending more radially outward than the brace-side frame attachment hole from the other side in the user width direction of the cylindrical part 56.

As shown in FIGS. 2 to 4, in the present embodiment, the internally threaded member 52 is inserted into the brace-side attachment hole from the side close to the user's thigh inserted into the thigh attachment 11, and the externally threaded member 55 is screwed to the internally threaded member 52 from the side far from the user's thigh.

Reference number 54a in FIGS. 3 and 4 is a radially outward projection that is provided on the flange part 53 and that engages with a depression 22 (see FIG. 3) formed in the inner connecting piece 21b, and thereby the internally threaded member 52 is retained so as to be incapable of relative rotation around the axis line relative to the inner connecting piece 21b (i.e., the thigh frame 20).

In the present embodiment, a swinging position of the lower leg frame 40 around the brace-side pivot axis line X at the time when the user's lower leg is extended until a maximum extending state defines a swinging end of the lower leg frame 40 toward the forward direction around the brace-side pivot axis line X relative to the thigh frame 20.

Specifically, as shown in FIG. 3, an upper-end surface 45 of the lower leg frame 40 (the end surface facing the thigh frame 20) is a sloped surface such that the radial distance from the brace-side pivot axis line X increases from one side toward the other side around the brace-side pivot axis line X, and a lower-end surface 25 of the thigh frame 20 (the end surface facing the lower leg frame 40) is a sloped surface corresponding to the upper-end surface 45 of the lower leg frame 40.

Due to this configuration, at the time when the user's lower leg is extended until a maximum extending state, the lower leg frame 40 rotates only toward one side around the brace-side pivot axis line X relative to the thigh frame 20 (in the direction in which the user's lower leg is bent relative to the thigh) and does not rotate toward the other side (in the direction in which the user's lower leg is extended relative to the thigh).

In the present embodiment, as shown in FIGS. 1 to 4, the knee-ankle-foot orthosis 1 further has a locking member 70 for inhibiting the rotation of the lower leg frame 40 toward both directions around the brace-side pivot axis line X relative to the thigh frame 20.

The locking member 70 is configured so as to be capable of reaching a locked state (the state shown in FIG. 2) where the thigh frame 20 and the lower leg frame 40 are surrounded by the locking member 70 to connect both frames 20, 40 and prevent the lower leg frame 40 from being relatively rotated around the brace-side pivot axis line X relative to the thigh frame 20, and a cancelled state where connection between the thigh frame 20 and the lower leg frame 40 is cancelled to permit the lower leg frame 40 to be relatively rotated around the brace-side pivot axis line X relative to the thigh frame 20.

In the present embodiment, the locking member 70 has a first locking member 70(1) acting on the first thigh frame 20(1) and the first lower leg frame 40(1), and a second locking member 70(2) acting on the second thigh frame 20(2) and the second lower leg frame 40(2).

In the present embodiment, as shown in FIG. 1, the knee-ankle-foot orthosis 1 further has a foot frame 60 on which a user places a foot.

In this case, the lower end portion of the lower leg frame 40 is connected to the foot frame 60.

Below, the gait motion assisting apparatus 100A according to the present embodiment will now be described.

Figure 5:
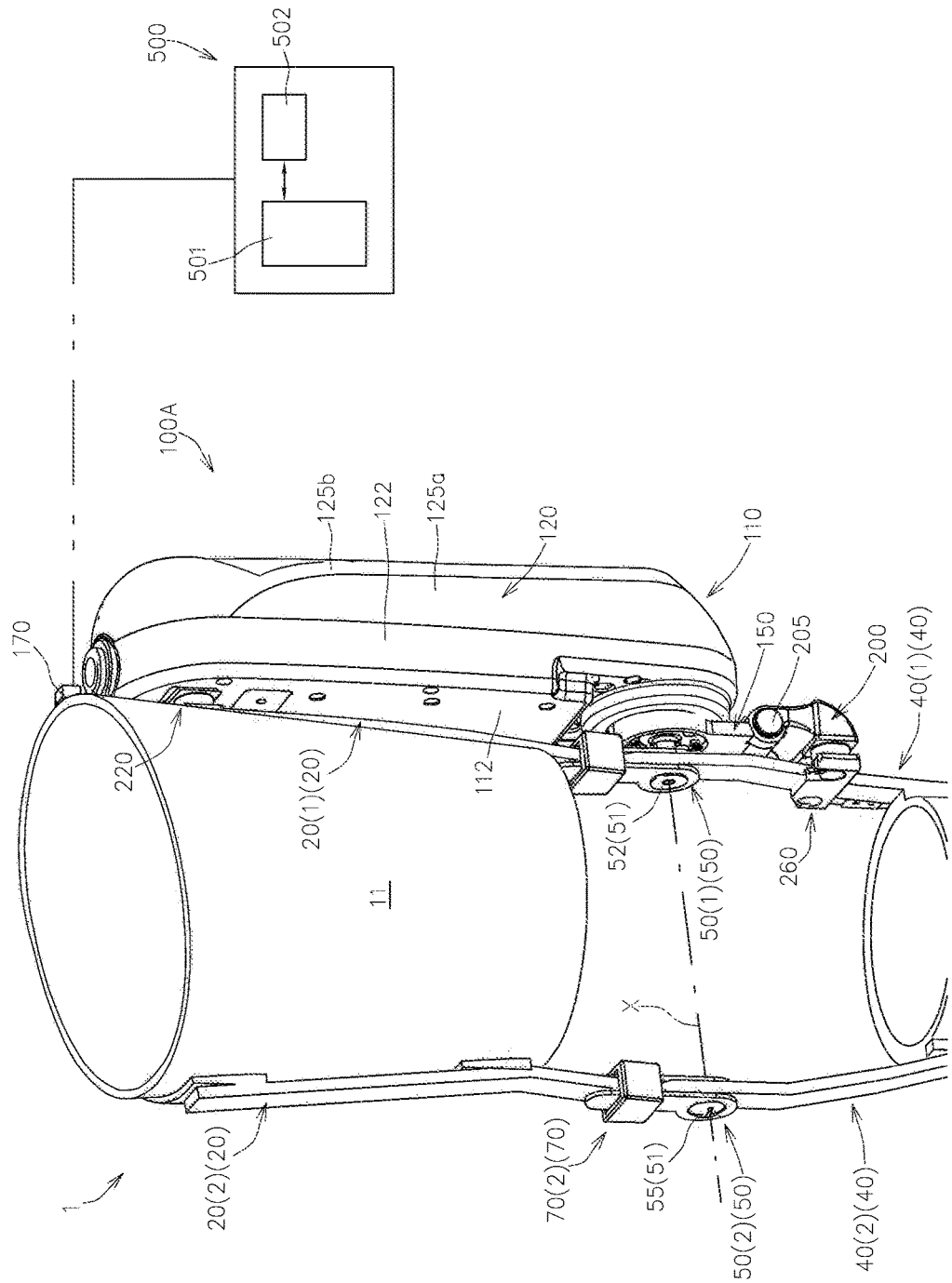
FIG. 5 is a perspective view of an attached state in which a gait motion assisting apparatus according to one embodiment of the present invention is attached to the knee-ankle-foot orthosis as viewed from an inner side in the user width direction and a forward side in the user front-back direction.

FIG. 5 is a perspective view of the gait motion assisting apparatus 100A attached to the knee-ankle-foot orthosis 1 as viewed from the inner side in the user width direction and the forward side in the user front-back direction.

FIG. 6 is an exploded perspective view of the gait motion assisting apparatus 100A as viewed from a side facing the knee-ankle-foot orthosis 1.

Figure 7:
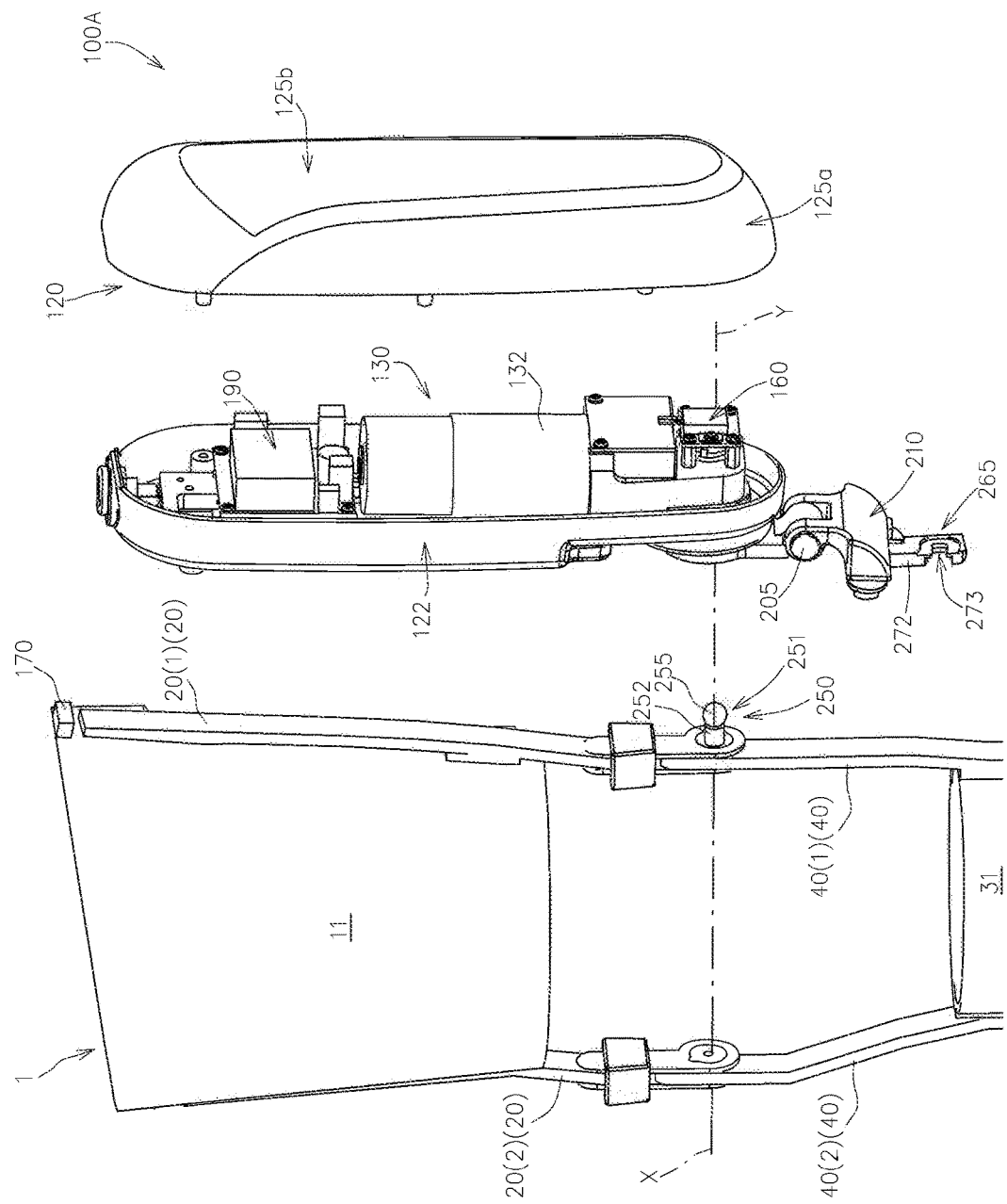
FIG. 7 is an exploded perspective view of the gait motion assisting apparatus and the knee-ankle-foot orthosis as viewed from an outer side in the user width direction.
Figure 8:
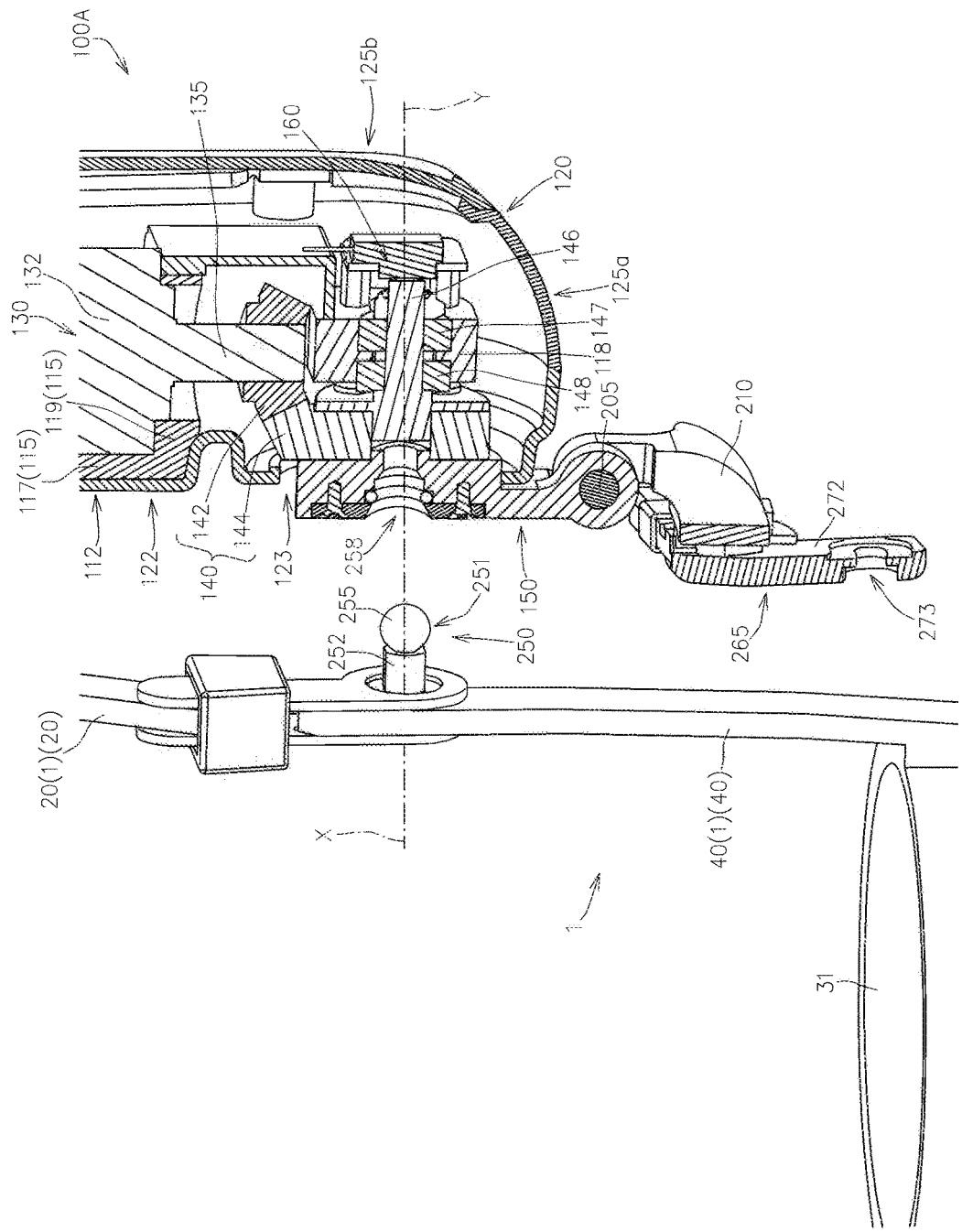
FIG. 8 is an exploded vertical cross-sectional view of the gait motion assisting apparatus and the knee-ankle-foot orthosis.

FIGS. 7 and 8 are an exploded perspective view and an exploded vertical cross-sectional view, respectively, of the gait motion assisting apparatus 100A and the knee-ankle-foot orthosis 1 as viewed from the inner side in the user width direction and the forward side in the user front-back direction.

As shown in FIGS. 1 to 3, the gait motion assisting apparatus 100A includes a casing 110, an electric motor 130 stored in the casing 110, a driving arm 150 operatively driven and swung by the electric motor 130, a rotation angle sensor 160 for detecting a swinging position of the driving arm 150, a gait motion state detecting sensor 170 for detecting a gait motion state during a gait cycle, and a control device 500 performing operational control of the electric motor 130.

The casing 110 has a frame 115 supporting the electric motor, and a cover 120 defining an accommodating space for the frame 115 and the electric motor 130.

The frame 115 includes a vertical-direction extending wall 117 extending substantially vertically while being along the user front-back direction at the time when the casing 110 is attached to the knee-ankle-foot orthosis 1, and a horizontal-direction extending wall 119 extending substantially horizontally from the vertical-direction extending wall 117.

As shown in FIG. 6, in the present embodiment, the horizontal-direction extending wall 119 extends outward in the user width direction from a lower end portion of the vertical-direction extending wall 117.

In the present embodiment, the frame 115 further includes a supporting wall 118 extending downward from the horizontal-direction extending wall 119 while being along the user front-back direction.

The cover 120 includes a lower cover 122 forming a facing surface 112 that faces the first thigh frame 20(1), and an upper cover 125 detachably connected to the lower cover 122 so as to form the accommodating space in cooperation with the lower cover 122.

In the present embodiment, the frame 115 is fixed within the accommodating space by connecting the vertical-direction extending wall 117 to an inner surface of the lower cover 122 via fastening members such as bolts.

In the present embodiment, the upper cover 125 includes a first upper cover 125*a* detachably connected to the lower cover 122, and a second upper cover 125*b* detachably connected to the first upper cover 125*a*.

The electric motor 130 includes a motor body 132 and an output shaft 135 connected to the motor body 132, and is configured so as to output driving force in both rotational directions including a first direction that is one side around an axial line and a second direction that is the other side around the axial line.

The motor body 132 is supported by the frame 115.

As shown in FIG. 6, in the present embodiment, the motor body 132 is mounted on the horizontal-direction extending wall 119.

The output shaft 135 extends downward from the motor body 132 across the horizontal-direction extending wall 119.

The gait motion assisting apparatus 100A further includes a driving source 190 for the electric motor 130 such as a battery.

In the present embodiment, as shown in FIGS. 6 and 7, the driving source 190 is supported by the vertical-direction extending wall 117 so as to be arranged above the electric motor 130.

The driving arm 150 is operatively connected to the output shaft 135, and is swung in a first direction that is one side and a second side that is the other side around an actuator-side pivot axis line Y in response to the driving force in the first and second directions of the output shaft 135.

As shown in FIG. 8, in the present embodiment, the driving arm 150 is operatively connected to the output shaft 135 via a gear transmission mechanism 140.

The gear transmission mechanism 140 includes a driving-side bevel gear 142 supported by the output shaft 135 so as to be incapable of relative rotation, and a driven-side bevel gear 144 arranged coaxially with the actuator-side pivot axis line Y while being engaged with the driving-side bevel gear 142.

The driven-side bevel gear 144 is arranged closer to the knee-ankle-foot orthosis 1 in the user width direction W than the output shaft 135 is.

The proximal end portion of the driving arm 150 is connected to the driven-side bevel gear 144 so that the driving arm 150 is swung around the actuator-side pivot axis line Y in response to the driving power of the output shaft 135.

As shown in FIG. 8, the lower cover 122 is provided with an access opening 123. The driven-side bevel gear 144 and the proximal end portion of the driving arm 150 are connected to each other via the access opening 123.

A distal end portion of the driving arm 150 is operatively connected to the first lower leg frame 40(1) in a state that the gait motion assisting apparatus 100A is attached to the knee-ankle-foot orthosis 1 so that the driving arm 150 presses the first lower leg frame 40(1) around the brace-side pivot axis line X in response to the swing of the driving arm 150 around the actuator-side pivot axis line Y.

The operative connecting structure between the distal end portion of the driving arm 150 and the first lower leg frame 40(1) will be described below.

In the present embodiment, as shown in FIG. 8, a detected shaft 146 is connected to the driven-side bevel gear 144 so as to be incapable of relative rotation around the actuator-side pivot axis line Y The rotation angle sensor 160 is arranged to detect a rotation angle of the detected shaft 146 around the axis line.

As shown in FIG. 8, the detected shaft 146 is supported by the supporting wall 118 via a bearing member 147.

Specifically, the supporting wall 148 is provided with a bearing hole opened in the user width direction, and the detected shaft 146 is supported by the bearing member 147 inserted into the bearing hole.

Figure 9:
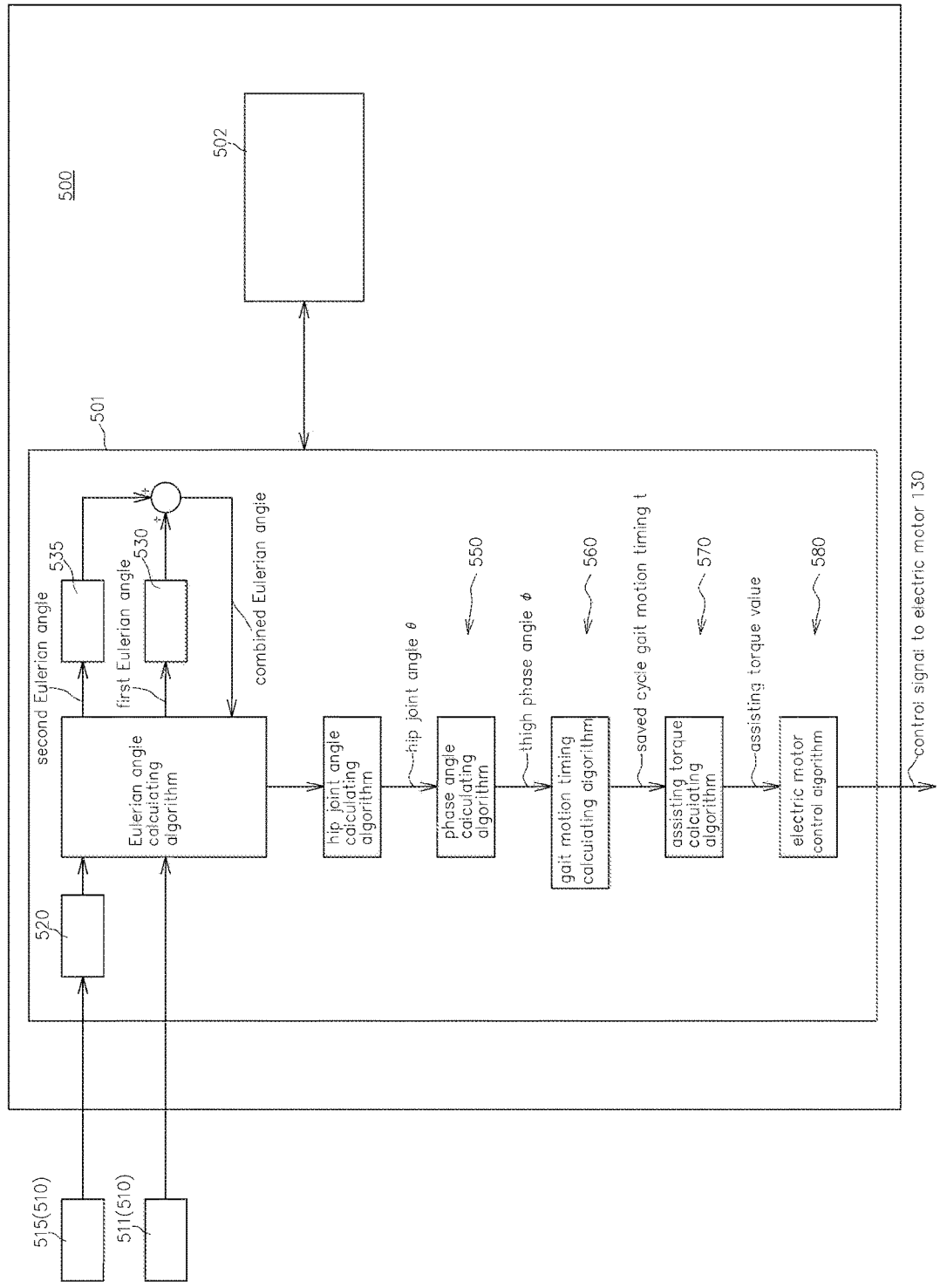
FIG. 9 is a control block diagram of the gait motion assisting apparatus.

FIG. 9 shows a control block diagram of the gait motion assisting apparatus.

The gait motion assisting apparatus 100A includes a thigh orientation detecting means as the gait motion state detecting sensor 170. The control device 500 recognizes a gait motion state during gait cycle based on a thigh phase angle, and performs operational control for the electric motor 130 such that gait assisting force suitable for the gait motion state is imparted.

That is, the gait motion assisting apparatus 100A is configured to detect movement of not the lower leg that is a control target site but the thigh that is a site different from the lower leg, and impart gait assisting force to the lower leg that is a control target site based on movement of the thigh.

The thigh orientation detecting means is capable of detecting an angle-related signal relating to a hip joint angle that is a front-back swing angle of a user's thigh.

As shown in FIG. 9, the control device 500 acts as a thigh phase angle calculating means 550 for calculating a thigh phase angle based on the angle-related signal; a gait motion timing calculating means 560 for converting the thigh phase angle into a gait state (a gait motion timing) during gait cycle; an assisting torque calculating means 570 for calculating a torque value that should be output at the gait motion timing; and an electric motor control means 580 responsible for operational control for the electric motor.

Specifically, as shown in FIG. 9, the control device 500 has a control part 501 including a control processing means for executing processing based on a signal received from the thigh orientation detecting means 510, a manually operated member or the like; and an actuator-side storage part 502 including a ROM storing a control program, control data and the like, a non-volatile storage means storing a setting value or the like such that the setting value or the like is not lost even when a power supply is interrupted and is rewritable, a RAM temporarily storing data generated during processing by the processing part or the like.

The thigh orientation detecting means 510 detects the angle-related signal at each predetermined specific sampling timing during a gait cycle.

The thigh orientation detecting means 510 may have various forms such as a gyro sensor, an acceleration sensor and a rotary encoder as long as it can directly or indirectly detect the front-back swing angle of the thigh (the hip joint angle).

For example, the thigh orientation detecting means 510 can be configured to have only an acceleration sensor, and in this case, the thigh phase angle during walking can be calculated from the acceleration (or position) and speed of the acceleration sensor without calculating the hip joint angle.

In the present embodiment, the thigh orientation detecting means 510 has a triaxial angular velocity sensor (a gyro sensor) 511 capable of detecting the front-back swing angle velocity of the thigh. The thigh phase angle calculating means 550 calculates the hip joint angle, which is the front-back swing angle of the thigh, by integrating the angular velocity of the thigh detected by the triaxial angular velocity sensor 511.

As shown in FIG. 9, the gait motion assisting apparatus according to the present embodiment is provided with a triaxial acceleration sensor 515. The thigh phase angle calculating means 550 is configured to calculate the hip joint angle (the front-back swing angle of the thigh) in which the vertical axis line that the triaxial acceleration sensor 515 detects when the user is in a standstill is the reference value.

The thigh phase angle calculating means 550, at every sampling timing, calculates a hip joint angle θ and, also, differentiates it to calculate a hip joint angular velocity ω.

For example, the thigh phase angle calculating means 550 calculates a hip joint angle θk at the $k^{th}$ sampling timing Sk (k is an integer of 1 or greater) from a gait cycle reference timing, and then differentiates it to calculate a hip joint angular velocity ωk at the sampling timing Sk.

Then, the thigh phase angle calculating means 550 calculates a thigh phase angle φk (=−Arctan(φk/θk) at the sampling timing Sk based on the hip joint angle θk and the hip joint angular velocity θk at the sampling timing Sk.

The gait motion timing calculating means 560 has a phase pattern function that defines a relationship between a thigh phase angle φ and a gait motion timing during gait cycle, and applies the thigh phase angle φ at a sampling timing sent from the thigh phase angle calculating means 550 to the phase pattern function to calculate which gait motion timing during gait cycle said the sampling timing corresponds to (which timing the sampling timing of the thigh phase angle φ corresponds to, when a gait cycle is 100%).

The assisting torque calculating means 570 applies a gait motion timing tk sent from the gait motion timing calculating means 560 to an assisting force control date that is saved in the control device 500 and that defines a relationship between a gait motion timing during gait cycle and a torque value to be output, to calculate a torque value that should be output at the sampling timing Sk.

As described above, the gait motion assisting apparatus 100A according to the present embodiment is configured to be attachable to both the knee-ankle-foot orthosis 1 for right use and the knee-ankle-foot orthosis 1 for left use.

Therefore, the control device 500 has, as the assisting force control date, an assisting force control date for right use and an assisting force control date for right use that are used in a case when the gait motion assisting apparatus 100A is attached to the knee-ankle-foot orthosis 1 for right use and the knee-ankle-foot orthosis 1 for left use, respectively.

The driver control means 580 executes operational control for the driver such that assisting force having a torque value calculated by the assisting torque calculating means 570 is output.

Thus, the gait motion assisting apparatus 100A is configured so as to calculate a gait state (a gait motion timing) during gait cycle based on a thigh phase angle φ, and output assisting force corresponding to the gait state.

Accordingly, assisting force suitable for a gait state during gait cycle can be output.

Moreover, the gait motion assisting apparatus 100A is configured to recognize a gait state (a gait motion timing) during gait cycle based on the thigh phase angle φ and then impart gait assisting force to the lower leg by the electric motor 130.

Accordingly, suitable gait assisting force can be supplied also to a user with hemiplegia due to a stroke or the like.

That is, conventional gait assisting devices configured to impart gait assisting force by a driver such as an electric motor are configured to detect movement of a control target site itself to which assisting force is to be imparted by the driver, and perform operational control for the driver based on the detection result.

For example, in conventional gait assisting devices that supply gait assisting force to the thigh, operational control for a driver that imparts gait assisting force to the thigh is performed based on the result of detecting thigh movement.

Also, in conventional gait assisting devices that supply gait assisting force to the lower leg, operational control for a driver that imparts gait assisting force to the lower leg is performed based on the result of detecting lower leg movement.

However, in the case of a patient with hemiplegia due to a stroke or the like, gait motion of the lower leg (front-back swing motion around the knee joint) often cannot be performed normally, while gait motion of the thigh (front-back swing motion around the hip joint) can be performed relatively normally.

When attempting to impart gait assisting force to the lower leg of such a patient, in the above conventional gait assisting devices, operational control for a driver that provides gait assisting force to the lower leg is performed based on the movement of the lower leg that is incapable of normal gait motion and, possibly, suitable gait assisting force cannot be provided.

On the other hand, the gait motion assisting apparatus 100A according to the present embodiment is configured to perform operational control for the driver 110 that imparts gait assisting force to the lower leg based on the thigh phase angle φ as described above.

Accordingly, even in the case of a user with hemiplegia due to a stroke or the like, suitable gait assisting force can be supplied to the lower leg.

Next, the mounting structure of the gait motion assisting apparatus 100A to the knee-ankle-foot orthosis 1 will now be described.

The gait motion assisting apparatus 100A according to the present embodiment includes an upper connecting mechanism 220, a lower connecting mechanism 260 and an intermediate connecting mechanism 250, and is configured to be detachably mounted to the knee-ankle-foot orthosis 1 by the three connecting mechanisms.

First, the intermediate connecting mechanism 250 will be described.

The intermediate connecting mechanism 250 is configured so as to connect an intermediate part of the gait motion assisting apparatus 100A in the vertical direction to the knee-ankle-foot orthosis 1 while having the actuator-side pivot axis line Y arranged coaxially with the brace-side pivot axis line X.

As shown in FIG. 8, the intermediate connecting mechanism 250 includes a ball stud 251 arranged at the knee-ankle-foot orthosis 1, and an accommodation depression 258 that is provided on a component of the gait motion assisting apparatus 100A so as to open toward the knee-ankle-foot orthosis 1 on the actuator-side pivot axis line Y, wherein the ball stud 251 and the accommodation depression 258 forms a ball joint structure.

As shown in FIG. 8, the ball stud 251 is arranged at the knee-ankle-foot orthosis 1 so as to extend outward in the user width direction on the brace-side pivot axis line X.

Specifically, the ball stud 251 includes a shaft part 252 extending in a direction toward the gait motion assisting apparatus 100A on the brace-side pivot axis line X, and a spherical head part 255 provided at the distal end portion of the shaft part 252.

In the present embodiment, the ball stud 251 is provided on the knee-ankle-foot orthosis 1 in a projecting manner by utilizing the brace-side connector 51.

Specifically, as shown in FIGS. 4 and 8, the ball stud 251 is provided on the knee-ankle-foot orthosis 1 in a projecting manner by being screw-connected to an inner-side threaded member (the internally threaded member 52 in the present embodiment) positioned on the inner side in the user width direction among the internally threaded member 52 and the externally threaded member 55 in the swinging connector 51 in place of an outer-side threaded member (the externally threaded member 55 in the present embodiment) positioned on the outer side in the user width direction among the internally threaded member 52 and the externally threaded member 55.

The ball stud 251 and the inner-side threaded member are realized by various configurations.

For example, the ball stud 251 may be formed with an axial stepped hole passing through in the axial line direction. The axial stepped hole includes a large-diameter portion open toward a side on which the spherical head part 255 is positioned, a small-diameter portion open toward a side far away from the spherical head part 255 in the axial line direction, and a step connecting the large-diameter portion and the small-diameter portion. The ball stud 251 and the inner-side threaded member can be connected to each other by a fastening member such as a bolt inserted in the axial stepped hole and fastened to the inner-side threaded member.

According to this configuration, the ball stud 251 can be easily provided on the existing knee-ankle-foot orthosis 1 in a projecting manner so as to be coaxial with the brace-side pivot axis line X.

The accommodation depression 258 is arranged at an innermost power-transmitting member among the components forming the transmission mechanism 140 and the driving arm 150 that is arranged coaxially with the actuator-side pivot axis line Y and is accessible from the inner side in the user width direction.

As described above in the present embodiment, the proximal end portion of the driving arm 150 is connected to the driven-side bevel gear 144 arranged coaxially with the actuator-side pivot axis line Y via the access opening 123 in the lower case 122.

In this case, the driving arm corresponds to the innermost power-transmitting member.

Accordingly, as shown in FIG. 8, the accommodation depression 258 is formed in the proximal end portion of the driving arm 150 so as to be arranged coaxially with actuator-side pivot axis line Y and open toward the knee-ankle-foot orthosis 1.

In comparison with the conventional gait motion assisting apparatus, the configuration makes it possible to reduce the size in the user width direction and also have the driving arm 150 come close to the lower leg frame 40 as much as possible so as to reduce the driving torque to be needed for pressing the lower leg frame 40.

Specifically, in the conventional gait motion assisting apparatus including a casing, an electric motor stored in the casing, a driving arm rotated and driven around an actuator-side pivot axis line by a rotational power operatively transmitted through a transmission mechanism from an output shaft of the electric motor, an upper connecting mechanism connecting an upper portion of the casing to the thigh frame, a lower connecting mechanism connection a distal end portion of the driving arm to the lower leg frame, and an intermediate connecting mechanism having the actuator-side pivot axis line arranged coaxially with the brace-side pivot axis line, the driving arm is supported by a driving shaft arranged on the brace-side pivot axis line and having a first end portion supported by an inner wall of the casing that faces the knee-ankle-foot orthosis and a second end portion supported by an outer wall of the casing that is opposite from the inner wall.

In the conventional gait motion assisting apparatus, a tubular convex portion provided in the knee ankle foot orthosis so as to be on the brace-side pivot axis line, and an accommodation depression is formed in a fixed plate fixed to an outer surface of the inner wall of the casing so as to be arranged on the brace-side pivot axis line and open toward the knee-ankle-foot orthosis.

According to the conventional configuration, it is needed to have a supporting structure for supporting the first end portion of the driving shaft in the inner wall of the casing, and also fix the fixed plate to the outer surface of the inner wall of the casing for securing such a thickness as to allow the accommodation depression to be formed. As a result, there is a problem that it is difficult to downsize the gait motion assisting device in the user width direction.

Furthermore, the proximal end portion of the driving arm is supported by an intermediate portion of the driving shaft in the axial line direction so that it is not possible to shorten the length between the proximal end portion of the driving arm and the lower leg frame in the user width direction. As a result, there is also a problem that a relatively large driving torque is needed to press the lower leg frame.

On the other hand, in the gait motion assisting apparatus according to the present embodiment, as described above, the accommodation depression 258 is formed in the innermost power-transmitting member among the components forming the transmission mechanism 140 and the driving arm 150 that is arranged coaxially with the actuator-side pivot axis line Y and is accessible from the inner side in the user width direction.

Accordingly, the gait motion assisting device 100A can be downsized in the user width direction, and allows the driving arm 150 to come close to the lower leg frame 40 in the user width direction as much as possible so as to reduce driving torque needed to press the lower leg frame 40.

Although, in the present embodiment, as described above, the driving arm 150 act as the innermost power-transmitting member and the accommodation depression 258 is formed in the driving arm, the present invention is not limited to the configuration.

Figure 10:
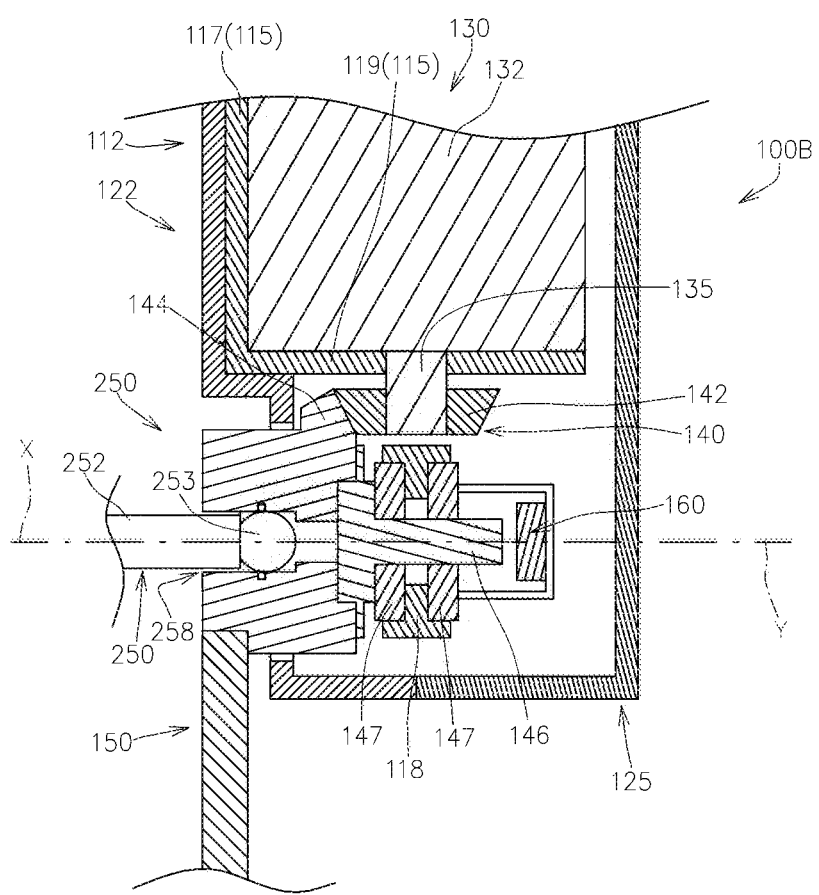
FIG. 10 is a partial vertical cross-sectional schematic view of a gait motion assisting apparatus according to a modification of the embodiment.

FIG. 10 is a partial vertical cross-sectional schematic view of a modification 100B of the present embodiment.

In the drawing, the same components as those in the present embodiment above are given the same reference numbers.

In the modification 100B shown in FIG. 10, the driven-side bevel gear 144 acts as the innermost power-transmitting member, and the accommodation depression is formed at an inner end surface of the driven-side bevel gear 144.

The thus configured modification 100B can realize the same effect as those of the present embodiment.

Next, the upper connecting mechanism 220 will be now described.

Figure 11:
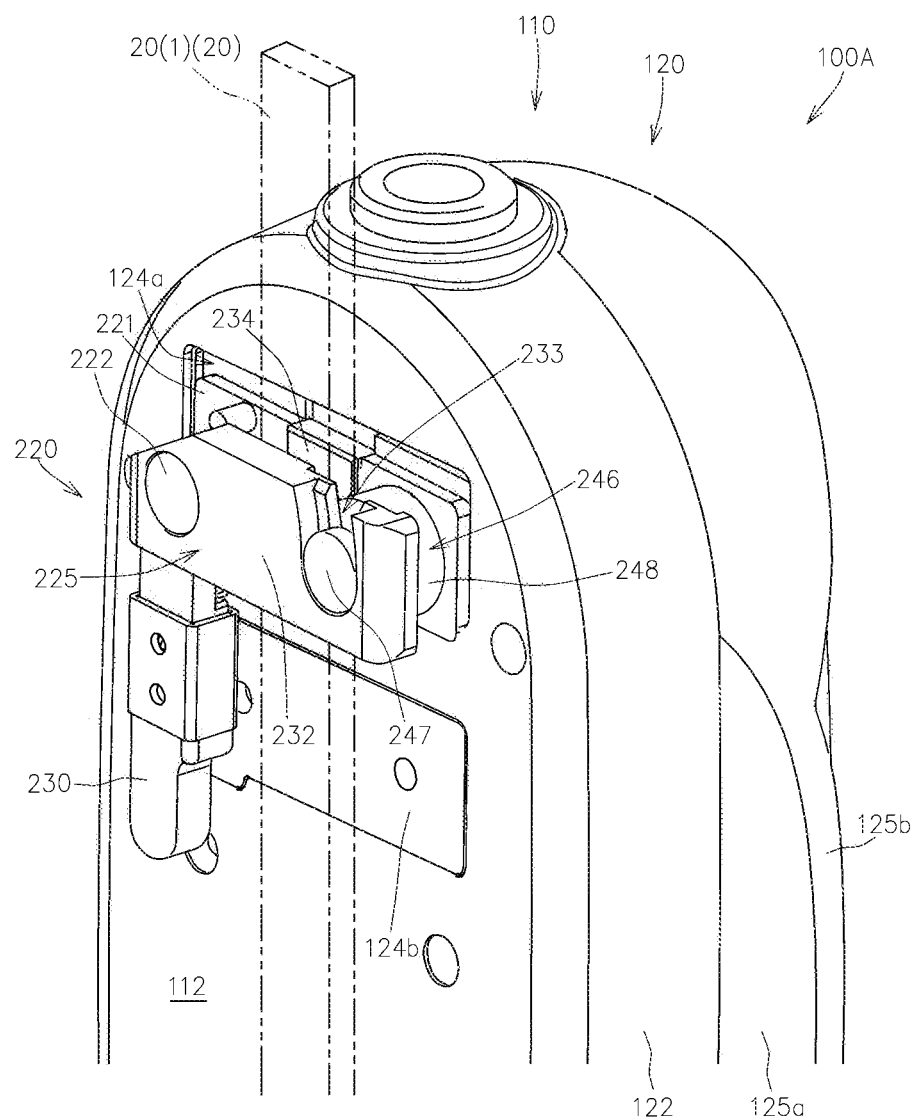
FIG. 11 is a perspective view of the vicinity of an upper connecting mechanism of the gait motion assisting apparatus, and shows a state in which an upper fastening member of the upper connecting mechanism is positioned in a fastening position.

FIG. 11 is a perspective view of the vicinity of the upper connecting mechanism 220.

In FIG. 11, the first thigh frame 20(1) is illustrated by the dashed double-dotted line.

As shown in FIG. 11, the upper connecting mechanism 220 includes an upper rotational shaft 222 provided on the facing surface 112 so as to extend inward in the user width direction and an upper fastening member 225 supported by the upper rotational shaft 222 so as to be rotatable around an axis line of the upper rotational shaft 222.

Figure 12:
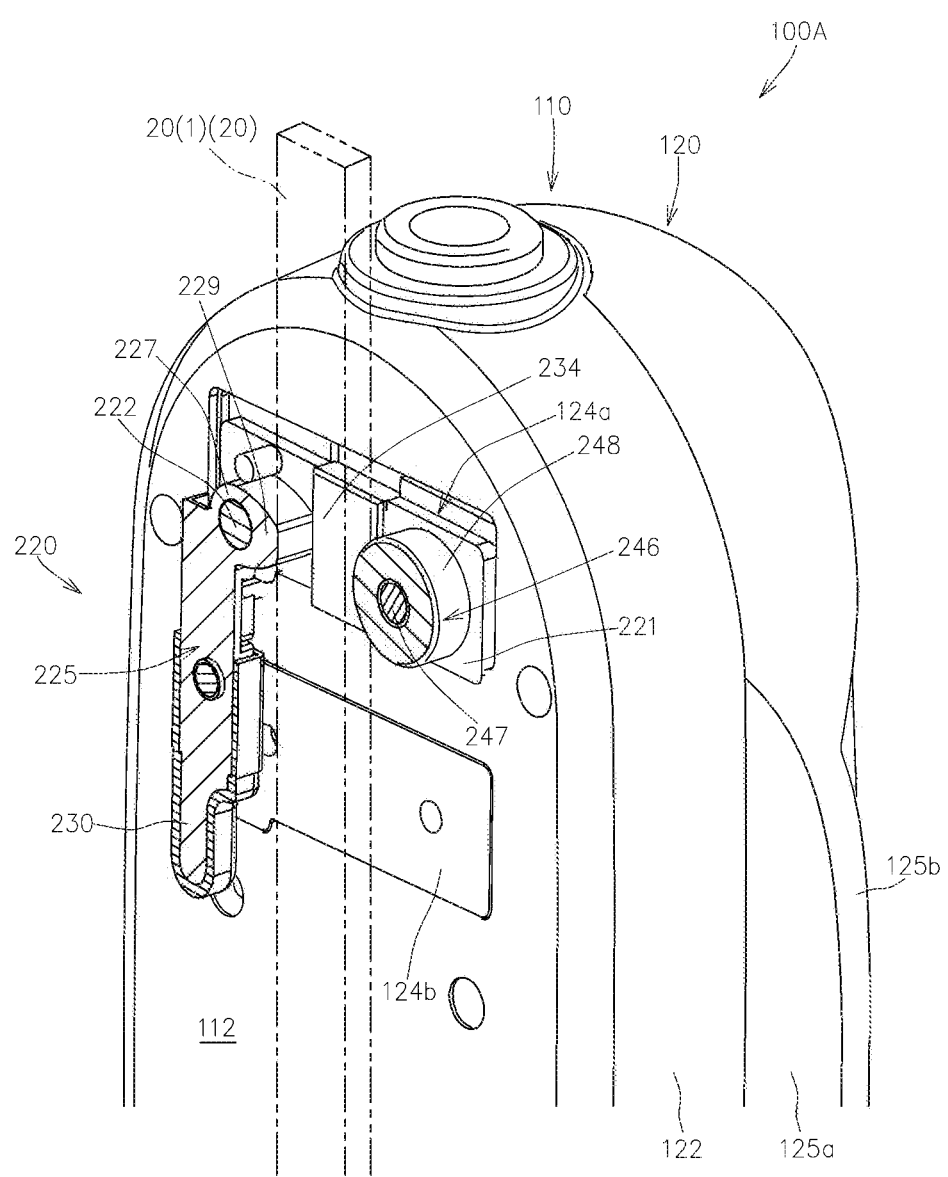
FIG. 12 is a vertical cross-sectional view of FIG. 11.

FIG. 12 is a perspective view of the vicinity of the upper connecting mechanism 220 with the upper fastening member 225 being cut in a vertical direction.

As shown in FIG. 12, the upper fastening member 225 includes a bearing part 227 supported by the upper rotational shaft 222 and a cam part 229 extending radially outward from the bearing part 227.

The cam part 229 is configured such that the radial distance between the outer circumferential surface and the axis line of the upper rotational shaft 222 is increased toward a first side around the axis line of the upper rotational shaft 222.

As shown in FIGS. 11 and 12, the upper connecting mechanism 220 further includes an upper receiving member 246 provided on the facing surface 112 at a position spaced apart in the user front-back direction from the upper rotational shaft 222 by a distance that enables the first thigh frame 20(1) to be interposed between the upper receiving member 246 and the upper rotational shaft 222.

In the present embodiment, the upper connecting mechanism 220 includes an upper receiving shaft 247 provided on the facing surface 112 so as to extend inward in the user width direction, and an elastic roller 248 supported by the upper receiving shaft 247 acts as the upper receiving member 246.

Figure 13:
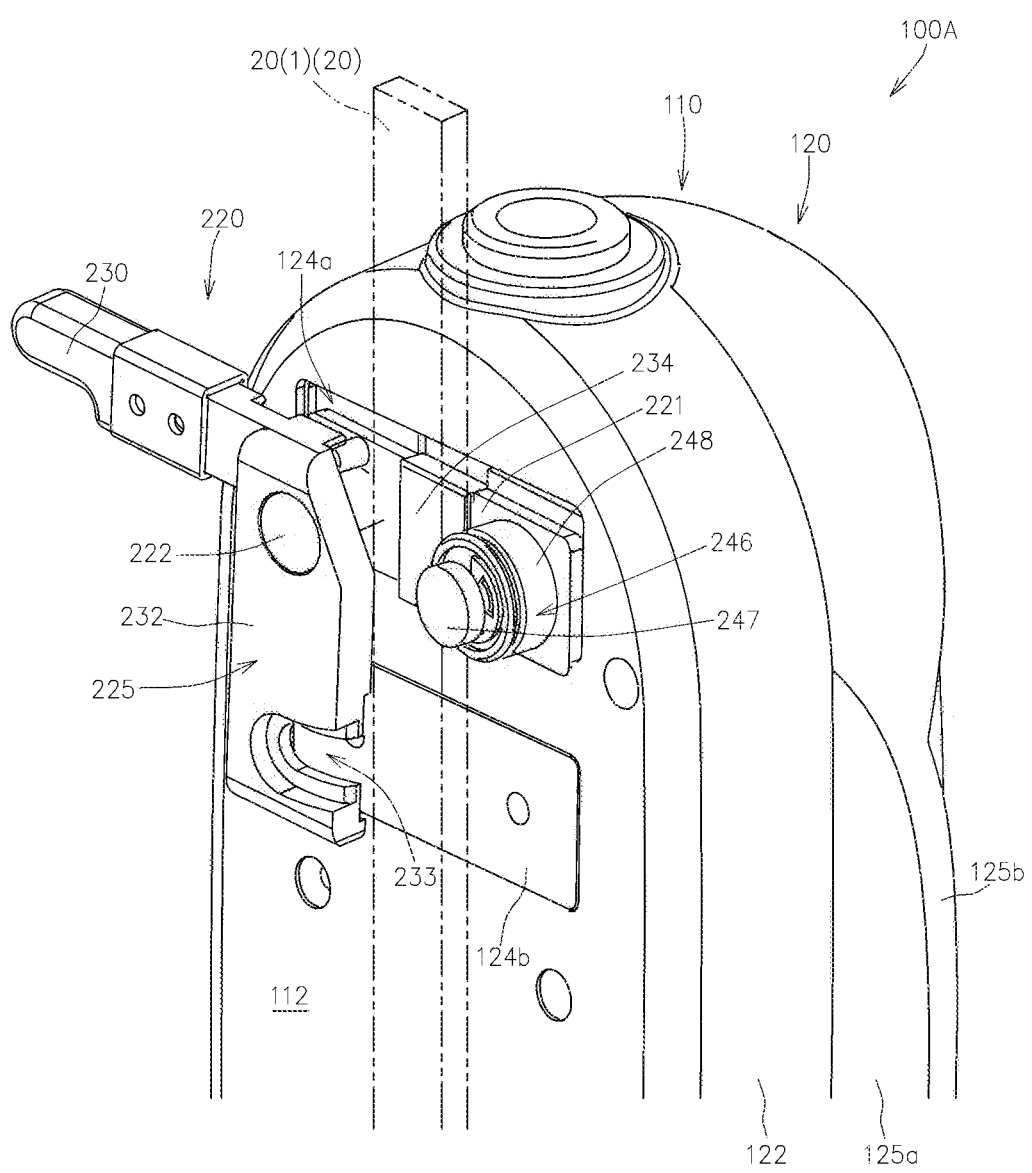
FIG. 13 is a perspective view corresponding to FIG. 11, and shows a state where the upper fastening member is positioned in a releasing position.
Figure 14:
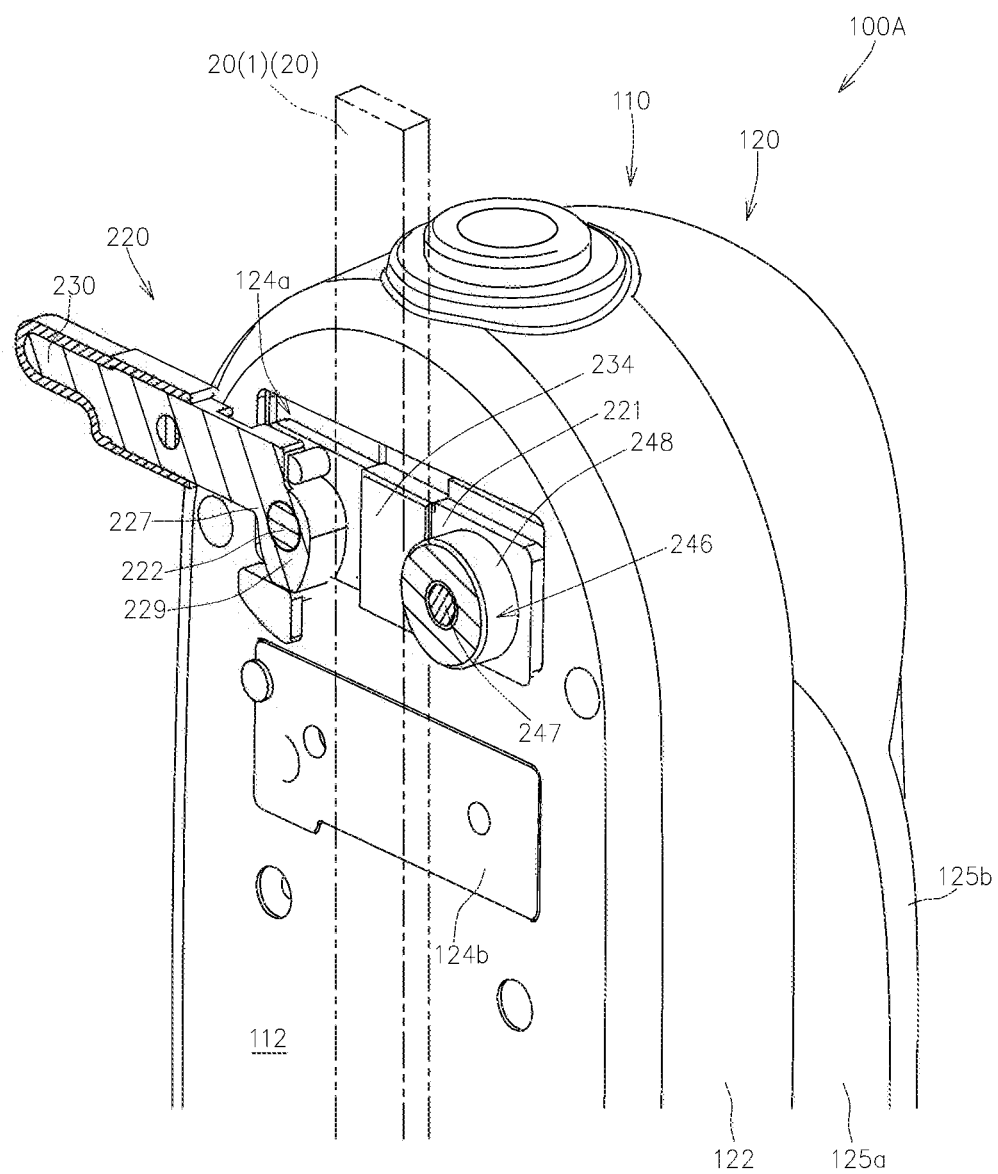
FIG. 14 is a vertical cross-sectional view of FIG. 13.

FIGS. 13 and 14 are perspective views corresponding to FIGS. 11 and 12, respectively, and show the state where the upper fastening member 225 is positioned in a predetermined releasing position around the upper rotational shaft 222.

As shown in FIGS. 13 and 14, in the state where the upper fastening member 225 is positioned in the releasing position around the upper rotational shaft 222, moving the gait motion assisting device 100A in a direction toward the knee-ankle-foot orthosis 1 enables the first thigh frame 20(1) to be positioned in the space between the upper fastening member 225 and the upper receiving member 246, and in the state where the first thigh frame 20(1) is positioned in the space, moving the gait motion assisting device 100A in a direction away from the knee-ankle-foot orthosis 1 enables the first thigh frame 20(1) to be retreated from the space.

Moreover, in the state where the first thigh frame 20(1) is positioned in the space, rotating the upper fastening member 225 from the releasing position (FIGS. 13 and 14) to a fastening position (FIGS. 11 and 12) around the upper rotational shaft 222 causes the cam part 229 to hold the first thigh frame 20(1) in cooperation with the upper receiving member 246 with respect to the user front-back direction, and thereby the state where the upper part of the gait motion assisting device 100A is connected to the first thigh frame 20(1) is attained.

As shown in FIGS. 11 to 14, in the present embodiment, the upper fastening member 225 further includes an operation arm 230 extending radially outward from the bearing part 227.

The operation arm 230 is configured such that the radial length between the free end of the operation arm 230 and the axis line of the upper rotational shaft 222 is greater than the radial length between the radially outermost end of the cam part 229 and the axis line of the upper rotational shaft 222.

This configuration, while making it easy to rotate the upper fastening member 225 around the upper rotational shaft 222 via the operation arm 230, makes it possible to effectively prevent connection between the upper part of the gait motion assisting device 100A and the first thigh frame 20(1) from being cancelled by the rotation of the upper fastening member 225 around the upper rotational shaft 222 via the cam part 229 when external force is unintentionally applied to the first thigh frame 20(1) and the upper part of the gait motion assisting device 100A.

As shown in FIGS. 11 and 13, in the present embodiment, the upper fastening member 225 has an engagement arm 232 extending radially outward from the bearing part 227 on the inner side in the user width direction than the cam part 229.

The engagement arm 232 is provided on the upper fastening member 225 so as to be positioned on the inner side in the user width direction than the first thigh frame 20(1) positioned in the space between the upper fastening member 225 and the upper receiving member 246.

The engagement arm 232 is provided with an engagement groove 238 for engagement with a portion of the upper receiving shaft 247, which extends more inward in the user width direction than the upper receiving member 246, when the upper fastening member 225 is rotated around the upper rotational shaft 222 from the releasing position to the fastening position around upper rotational shaft 222 so that the cam part 229 holds the first thigh frame 20(1) with respect to the user front-back direction in cooperation with the upper receiving member 246, and by the inward extending portion of the upper receiving shaft 247 inserted in the engagement groove 233, the unintentional relative movement of the upper part of the gait motion assisting device 100A and the first thigh frame 20(1) in the user width direction is prevented.

Reference number 234 in FIGS. 11 to 14 denotes a spacer for filling a gap existed between the first thigh frame 20(1) and the facing surface 112 of the gait motion assisting device 100A with respect to the user width direction when the first thigh frame 20(1) is positioned in the space between the upper fastening member 225 and the upper receiving member 246 and the upper fastening member 225 is positioned in the fastening position. The spacer is preferably a rubber body.

As shown in FIG. 6, in the present embodiment, the upper rotational shaft 222 and the upper receiving member 246 are supported by the vertical-direction extending wall 117. The lower cover 122 is formed with a through hole 124a that allows distal end portions of the upper rotational shaft 222 and the upper receiving member 246 to extend outward in a direction toward the knee-ankle-foot orthosis 1.

The thus configuration where the upper rotational shaft 222 and the upper receiving member 246 are supported by the frame 115 having a predetermined stiffness enough for supporting the electric motor 130 can ensure the strength of the upper connecting mechanism 220.

Also in the present embodiment, the upper rotational shaft 222 and the upper receiving member 246 can be supported by the vertical-direction extending wall 117 at a plurality of supporting positions that are displaced in the vertical direction.
different According to the configuration, it is possible to effectively adapt the upper connecting mechanism 220 to the thigh frames 20 of various knee-ankle-foot orthoses 1 that are custom-made according to the user's physiques.

That is, relative positions of the first thigh frame 20(1) and the thigh attachment 11 in knee-ankle-foot orthoses 1 that are custom-made according to the user's physiques are different to one another.

Regarding this point, enabling the upper rotational shaft 222 and the upper receiving member 246 to be supported at various supporting positions that are displaced to one another in the vertical direction among makes it possible to easily connect the upper connecting mechanism 220 to the various knee-ankle-foot orthoses 1 without interfering with the thigh attachment 11.

As shown in FIGS. 6 and 11 to 14, the lower cover 122 is formed with the plurality of through holes 124a corresponding to the plurality of supporting positions, respectively.

The through hole 124a among the plurality of through holes 124a that is not used for attaching the upper connecting mechanism 220 is closed by a closing plate 124b.

As shown in FIG. 8, in the gait motion assisting device 100A according to the present embodiment, the upper rotational shaft 222 and the upper receiving member 246 are supported by a plate 221, and the plate can be supported by the vertical-direction extending wall 117 at the plurality of supporting positions.

The configuration makes it possible to easily change the supporting position of the upper rotational shaft 222 and the upper receiving member 246.

Next, the lower connecting mechanism 260 will be now described.

Figure 15:
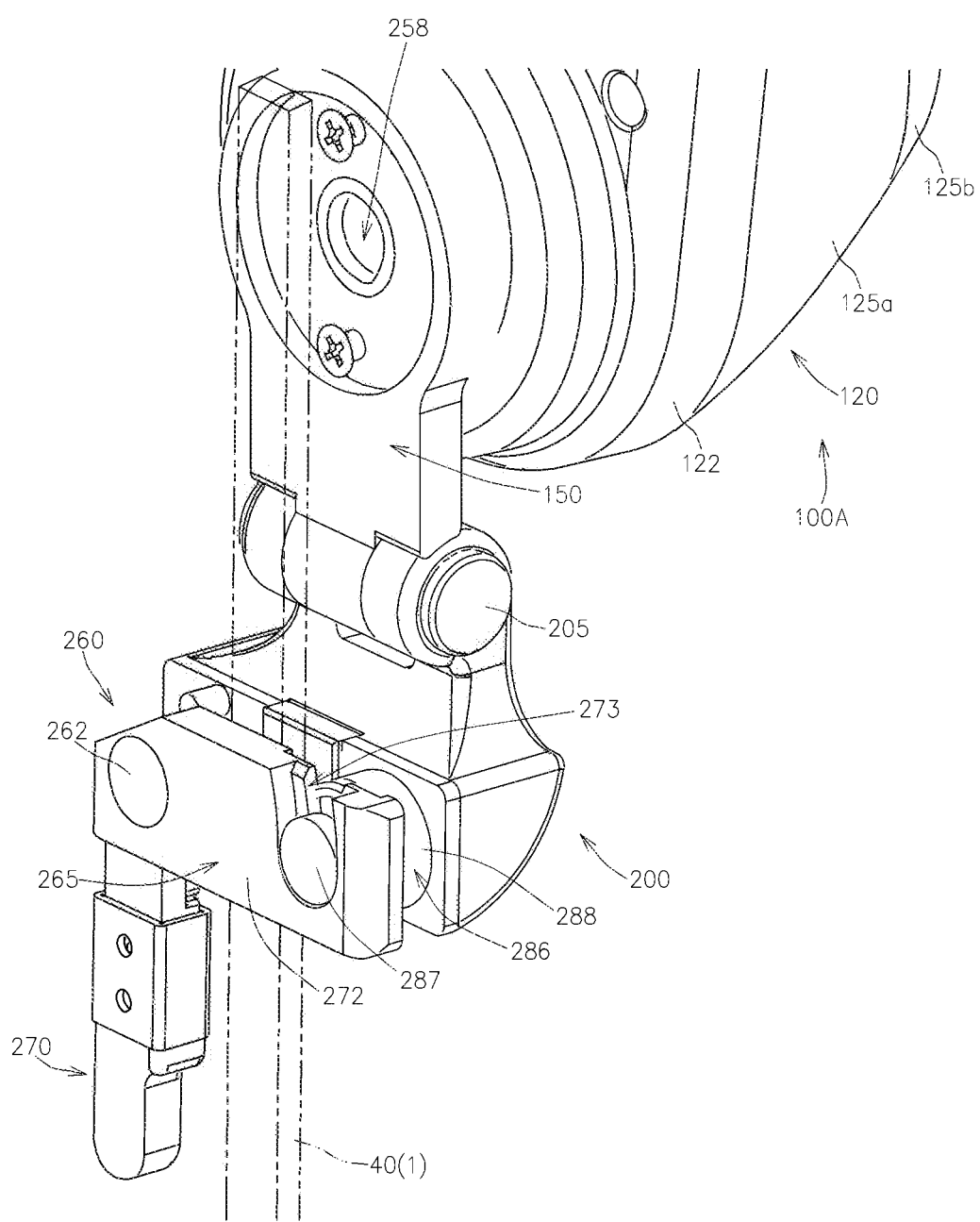
FIG. 15 is a perspective view of the vicinity of a lower connecting mechanism of the gait motion assisting apparatus, and shows a state where a lower fastening member of the lower connecting mechanism is positioned in a fastening position.

FIG. 15 shows a perspective view of the vicinity of the lower connecting mechanism 260.

In FIG. 15, the first lower leg frame 40(1) is illustrated by the dashed double-dotted line.

As shown in FIGS. 5 to 8 and 15, in the present embodiment, the distal end portion of the driving arm 150 is provided with a swinging member 200 capable of swinging around a rotational shaft 205 along the user front-back direction, and the lower connecting mechanism 260 is provided in the swinging member 200.

The configuration makes it possible to appropriately change the relative position of the lower connecting mechanism 260 with respect to the upper connecting mechanism 220 and the intermediate connecting mechanism 250 in the user width direction so that the gait motion assisting device 100A can be appropriately attached to the variously shaped knee-ankle-foot orthoses 1 that are custom-made according to the user's physique.

That is, the knee-ankle-foot orthosis 1 is custom-made according to the user's physique, and thus the tilt angle and/or the curvature of the first thigh frame 20(1) relative to the first lower leg frame 40(1) with respect to the user width direction W (see FIG. 1) is different for each knee-ankle-foot orthosis 1.

In this regard, adopting the configuration in which the swinging member 200 is connected to the distal end portion of the driving arm 150 so as to be capable of swinging in the user width direction and the lower connecting mechanism 260 is provided in the swinging member 200 enables the gait motion assisting device 100A to be appropriately attached to various knee-ankle-foot orthoses 1 having different tilt angles and/or curvatures of the first thigh frame 20(1) relative to the first lower leg frame 40(1) with respect to the user width direction W.

The lower connecting mechanism 260 has the substantially same configuration as the upper connecting mechanism 220.

Specifically, as shown in FIG. 15, the lower connecting mechanism 260 includes a lower rotational shaft 262 provided on the swinging member 200 so as to extend inward in the user width direction and a lower fastening member 265 supported by the lower rotational shaft 262 so as to be rotatable around an axis line of the lower rotational shaft 262.

Figure 16:
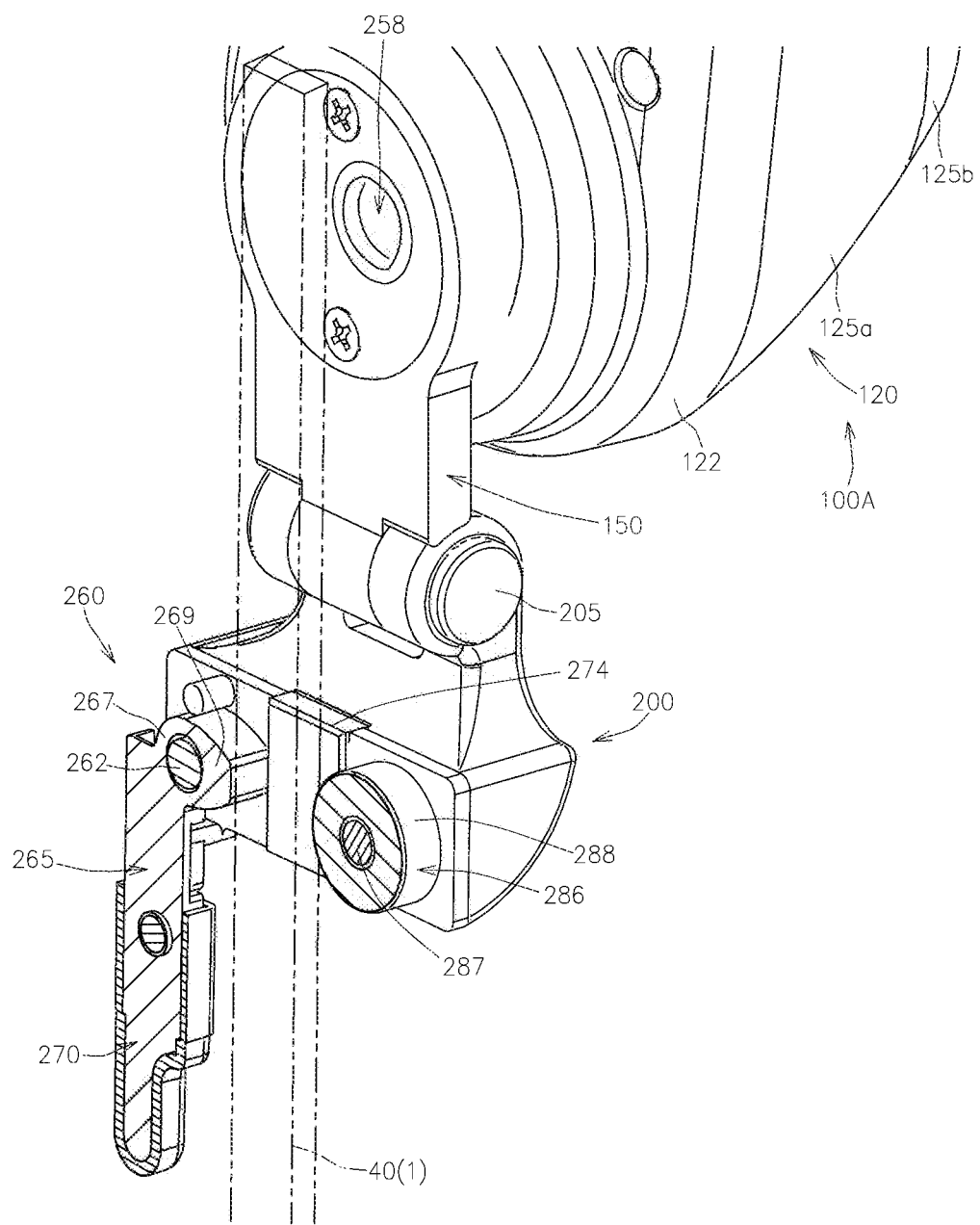
FIG. 16 is a vertical cross-sectional view of FIG. 15.

FIG. 16 is a perspective view of the vicinity of the lower connecting mechanism 260 with the lower fastening member 265 being cut in a vertical direction.

As shown in FIG. 16, the lower fastening member 265 includes a bearing part 267 supported by the lower rotational shaft 262 and a cam part 269 extending radially outward from the bearing part 267.

The cam part 269 is configured such that the radial distance between the outer circumferential surface and the axis line of the lower rotational shaft 262 is increased toward a first side around the axis line of the lower rotational shaft 262.

As shown in FIGS. 15 and 16, the lower connecting mechanism 260 further includes a lower receiving member 286 supported by the swinging member 200 at a position spaced apart in the user front-back direction from the lower rotational shaft 262 by a distance that enables the first lower leg frame 40(1) to be interposed between the lower receiving member 286 and the lower rotational shaft 262.

In the present embodiment, the lower connecting mechanism 260 includes a lower receiving shaft 287 provided on the swinging member 200 so as to extend inward in the user width direction, and an elastic roller 288 supported by the lower receiving shaft 287 acts as the lower receiving member 286.

Figure 17:
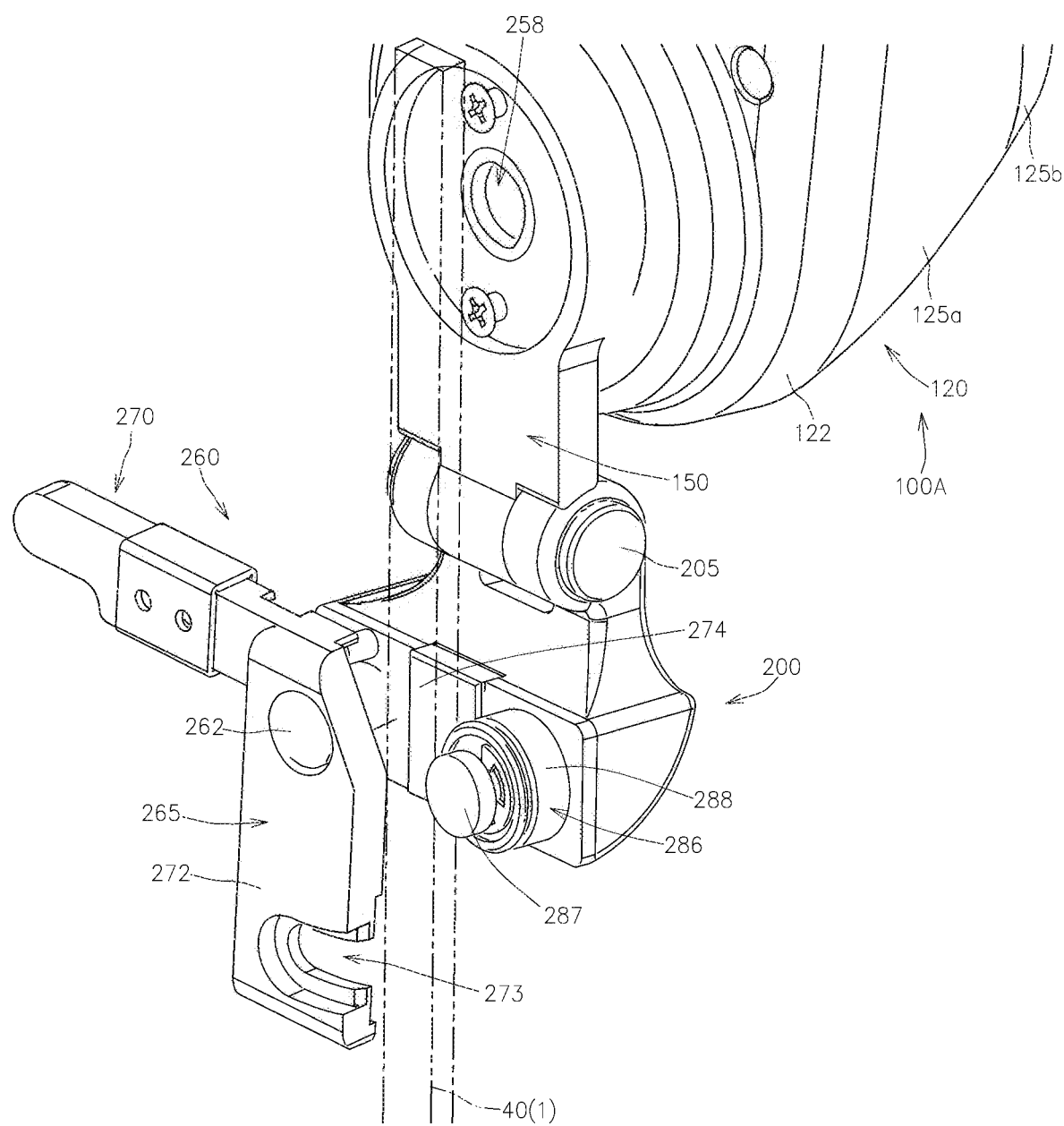
FIG. 17 is a perspective view corresponding to FIG. 15, and shows a state where the lower fastening member is positioned in a releasing position.

FIG. 17 is a perspective view corresponding to FIG. 1, and shows the state where the lower fastening member 265 is positioned in a predetermined releasing position around the lower rotational shaft 262.

As shown in FIG. 17, in the state where the lower fastening member 265 is positioned in the releasing position around the lower rotational shaft 262, moving the gait motion assisting device 100A in a direction toward the knee-ankle-foot orthosis 1 enables the first lower leg frame 40(1) to be positioned in the space between the lower fastening member 265 and the lower receiving member 286, and in the state where the first lower leg frame 40(1) is positioned in the space, moving the gait motion assisting device 100A in a direction away from the knee-ankle-foot orthosis 1 enables the first lower leg frame 40(1) to be retreated from the space.

Moreover, in the state where the first lower leg frame 40(1) is positioned in the space, rotating the lower fastening member 265 from the releasing position (FIG. 17) to a fastening position (FIGS. 15 and 16) around the lower rotational shaft 262 causes the cam part 269 to hold the first lower leg frame 40(1) in cooperation with the lower receiving member 286 with respect to the user front-back direction, and thereby the state where the lower part of the gait motion assisting device 100A is connected to the first lower leg frame 40(1) is attained.

As shown in FIGS. 15 to 17, in the present embodiment, the lower fastening member 265 further includes an operation arm 270 extending radially outward from the bearing part 267.

The operation arm 270 is configured such that the radial length between the free end of the operation arm 270 and the axis line of the lower rotational shaft 262 is greater than the radial length between the radially outermost end of the cam part 269 and the axis line of the lower rotational shaft 262.

This configuration, while making it easy to rotate the lower fastening member 265 around the lower rotational shaft 262 via the operation arm 270, makes it possible to effectively prevent connection between the lower part of the gait motion assisting device 100A and the first lower leg frame 40(1) from being cancelled by the rotation of the lower fastening member 265 around the lower rotational shaft 262 via the cam part 269 when external force is unintentionally applied to the first lower leg frame 40(1) and the lower part of the gait motion assisting device 100A.

As shown in FIGS. 15 to 17, in the present embodiment, the lower fastening member 265 has an engagement arm 272 extending radially outward from the bearing part 267 on the inner side in the user width direction than the cam part 269.

The engagement arm 272 is provided on the lower fastening member 265 so as to be positioned on the inner side in the user width direction than the first lower leg frame 40(1) positioned in the space between the lower fastening member 265 and the lower receiving member 286.

The engagement arm 272 is provided with an engagement groove 273 for engagement with a portion of the lower receiving shaft 287, which extends more inward in the user width direction than the lower receiving member 286, when the lower fastening member 265 is rotated around the lower rotational shaft 262 from the releasing position to the fastening position around lower rotational shaft 262 so that the cam part 269 holds the first lower leg frame 40(1) with respect to the user front-back direction in cooperation with the lower receiving member 286, and by the inward extending portion of the lower receiving shaft 287 inserted in the engagement groove 273, the unintentional relative movement of the lower part of the gait motion assisting device 100A and the first lower leg frame 40(1) in the user width direction is prevented.

Also, the lower connecting mechanism 260 is provided with a spacer for filling a gap existed between the first lower leg frame 40(1) and the swinging member 200 with respect to the user width direction when the first lower leg frame 40(1) is positioned in the space between the lower fastening member 265 and the lower receiving member 286 and the lower fastening member 265 is positioned in the fastening position.

DESCRIPTION OF THE REFERENCE NUMERALS

1 Knee-ankle-foot orthoses for right use and left use
11 Thigh attachment
20(1), 20(2) First and second thigh frames
31 Lower leg attachment
40(1), 40(2) First and second lower leg frames
100A, 100B Gait motion assisting apparatus
110 Casing
112 Facing surface
115 Frame
117 Vertical-direction extending wall
120 Cover
122 Lower cover
123 Access opening
124a Through hole
124b Closing plate
125 Upper cover
130 Electric motor
132 Motor body
135 Output shaft
140 Transmission mechanism
142 Driving-side bevel gear
144 Driven-side bevel gear
150 Driving arm
200 Swinging member
220 Upper connecting mechanism
221 Plate
222 Upper rotational shaft
225 Upper fastening member
227 Bearing part
229 Cam part
246 Upper receiving member
250 Intermediate connecting mechanism
251 Ball stud
258 Accommodation depression
260 Lower connecting mechanism
262 Lower rotational shaft
265 Lower fastening member
267 Bearing part
269 Cam part
286 Lower receiving member
X Brace-side pivot axis line
Y Actuator-side pivot axis line

The invention claimed is:

1. A gait motion assisting apparatus attachable to a knee-ankle-foot orthosis including a thigh attachment to which a user's thigh is attached, a thigh frame supporting the thigh attachment and extending in a substantially vertical direction, a lower leg attachment to which the user's lower leg is attached and a lower leg frame supporting the lower leg attachment and extending in a substantially vertical direction, the lower leg frame being rotatable relative to the thigh frame around a brace-side pivot axis line that is coaxial with a swing axis line of the user's knee joint, the gait motion assisting apparatus comprising, an electric motor, a casing housing the electric motor, a driving arm driven and rotated around an actuator-side pivot axis line by rotational power operatively transmitted via a transmission mechanism from an output shaft of the electric motor, an upper connecting mechanism connecting an upper part of the casing to the thigh frame, a lower connecting mechanism operatively connecting a distal end portion of the driving arm to the lower leg frame, and an intermediate connecting mechanism having the actuator-side pivot axis line arranged coaxially with the brace-side pivot axis line, wherein the intermediate connecting mechanism includes a ball stud arranged at the knee-ankle-foot orthosis so as to extend outward in the user width direction on the brace-side pivot axis line X, and an accommodation depression arranged so as to open toward the knee-ankle-foot orthosis on the actuator-side pivot axis line, the ball stud capable of being inserted into the accommodation depression, and wherein the accommodation depression is arranged at an innermost power-transmitting member among components forming the transmission mechanism and the driving arm that is arranged coaxially with the actuator-side pivot axis line and is accessible from the inner side in the user width direction.

2. The gait motion assisting apparatus according to claim 1, wherein
the casing includes a frame supporting the electric motor and a cover defining an accommodating space for the electric motor and the frame,
the cover includes a lower cover whose outer surface forms a facing surface facing the thigh frame in an attached state where the gait motion assisting apparatus is attached to the knee-ankle-foot orthosis and an upper cover detachably connected to the lower cover so as to form the accommodating space in cooperation with the lower cover,
the frame includes a vertical-direction extending wall extending substantially vertically in the attached state of the gait motion assisting apparatus and fixed to the lower cover,
the electric motor includes a motor body supported by the frame and an output shaft extending downward from the motor body,
the transmission mechanism includes a driving-side bevel gear supported by the output shaft so as to be incapable of relative rotation and a driven-side bevel gear that is positioned on a side more inward in the user width direction than the output shaft and arranged coaxially with the actuator-side pivot axis line while being engaged with the driving-side bevel gear,
the driving arm has a proximal end portion operatively connected to the driven-side bevel gear,
the lower cover is provided with an access opening that allows the driven-side bevel gear and the proximal end portion of the driving arm to be connected to each other, and
the accommodation depression is arranged at an inward surface of the proximal end portion of the driving arm in the user width direction.

3. The gait motion assisting apparatus according to claim 2, wherein
the upper connecting mechanism includes an upper rotational shaft extending inward in the user width direction, an upper receiving member spaced apart in the user front-back direction from the upper rotational shaft by a distance that enables the thigh frame to be interposed between the upper receiving member and the upper rotational shaft, and an upper fastening member rotatably supported by the upper rotational shaft so as to take a releasing position and a fastening position around the upper rotational shaft,
the upper fastening member includes a bearing part supported by the upper rotational shaft and a cam part extending radially outward from the bearing part, and
setting the upper fastening member in the releasing position enables the thigh frame to be entered into and retreated from the space, and rotating the upper fastening member from the releasing position to the fastening position in the state where the thigh frame is positioned in the space causes the cam part to hold the thigh frame in cooperation with the upper receiving member.

4. The gait motion assisting apparatus according to claim 3, wherein
the upper rotational shaft and the upper receiving member are supported by the vertical-direction extending wall, and
the lower cover is formed with a through hole that allows distal end portions of the upper rotational shaft and the upper receiving member to extend outward in a direction toward the knee-ankle-foot orthosis.

5. The gait motion assisting apparatus according to claim 4, wherein the vertical-direction extending wall is capable of supporting the upper rotational shaft and the upper receiving member at a plurality of supporting positions that are displaced in the vertical direction.

6. The gait motion assisting apparatus according to claim 5, further comprising a plate that supports the upper rotational shaft and the upper receiving member,
wherein the vertical-direction extending wall is capable of supporting the plate at the plurality of supporting positions.

7. The gait motion assisting apparatus according to claim 6, wherein
the lower cover is formed with the plurality of through holes corresponding to the plurality of supporting positions, respectively, and
one or plural of the plurality of through holes that is not used for attaching the upper connecting mechanism is closed by a closing plate.

8. The gait motion assisting apparatus according to claim 1, wherein
the lower connecting mechanism includes a lower rotational shaft extending inward in the user width direction, a lower receiving member spaced apart in the user front-back direction from the lower rotational shaft by a distance that enables the lower leg frame to be interposed between the lower receiving member and the lower rotational shaft, and lower fastening member rotatably supported by the lower rotational shaft so as to take a releasing position and a fastening position around the lower rotational shaft,
the lower fastening member includes a bearing part supported by the lower rotational shaft and a cam part extending radially outward from the bearing part, and
setting the lower fastening member in the releasing position enables the lower leg frame to be entered into and retreated from the space, and rotating the lower fastening member from the releasing position to the fastening position in the state where the lower leg frame is positioned in the space causes the cam part to hold the lower leg frame in cooperation with the lower receiving member.

9. The gait motion assisting apparatus according to claim 8, further comprising a swinging member capable of swinging around a rotational shaft along the user front-back direction in a state where the gait motion assisting apparatus is attached to the knee-ankle-foot orthosis,
wherein the lower connecting mechanism is supported by the swinging member.

* * * * *